(12) United States Patent
Yun et al.

(10) Patent No.: US 12,419,836 B2
(45) Date of Patent: Sep. 23, 2025

(54) EXTRACELLULAR VESICLES DERIVED FROM RECOMBINANT MICROORGANISM INCLUDING POLYNUCLEOTIDE ENCODING TARGET PROTEIN AND USE THEREOF

(71) Applicant: MEDYTOX INC., Cheongju-si (KR)

(72) Inventors: Ji Ae Yun, Suwon-si (KR); Hyun Uk Jeong, Suwon-si (KR); Jin Ho Choo, Bucheon-si (KR); Soo Min Song, Yongin-si (KR); Ji Yoon Song, Seongnam-si (KR); Yong In Kim, Seongnam-si (KR); Seung Kee Cho, Suwon-si (KR)

(73) Assignee: MEDYTOX INC., Cheongju-si (KR)

( * ) Notice: Subject to any disclaimer, the term of this patent is extended or adjusted under 35 U.S.C. 154(b) by 1359 days.

(21) Appl. No.: 17/052,319

(22) PCT Filed: May 3, 2019

(86) PCT No.: PCT/KR2019/005334
§ 371 (c)(1),
(2) Date: Nov. 2, 2020

(87) PCT Pub. No.: WO2019/212293
PCT Pub. Date: Nov. 7, 2019

(65) Prior Publication Data
US 2021/0169802 A1    Jun. 10, 2021

(30) Foreign Application Priority Data
May 4, 2018    (KR) ........................ 10-2018-0052157

(51) Int. Cl.
| | | |
|---|---|---|
| *A61K 9/127* | (2025.01) | |
| *A61K 8/14* | (2006.01) | |
| *A61K 8/64* | (2006.01) | |
| *A61K 8/9728* | (2017.01) | |
| *A61K 8/99* | (2017.01) | |
| *A61K 35/747* | (2015.01) | |
| *A61K 36/064* | (2006.01) | |
| *A61Q 17/04* | (2006.01) | |
| *A61Q 19/02* | (2006.01) | |
| *A61Q 19/08* | (2006.01) | |
| *C07K 14/475* | (2006.01) | |
| *C07K 14/485* | (2006.01) | |
| *C07K 14/495* | (2006.01) | |
| *C07K 14/50* | (2006.01) | |
| *C07K 14/54* | (2006.01) | |
| *C07K 14/65* | (2006.01) | |

(52) U.S. Cl.
CPC ............ *A61K 9/127* (2013.01); *A61K 8/14* (2013.01); *A61K 8/64* (2013.01); *A61K 8/9728* (2017.08); *A61K 8/99* (2013.01); *A61K 35/747* (2013.01); *A61K 36/064* (2013.01); *A61Q 17/04* (2013.01); *A61Q 19/02* (2013.01); *A61Q 19/08* (2013.01); *C07K 14/475* (2013.01); *C07K 14/485* (2013.01); *C07K 14/495* (2013.01); *C07K 14/50* (2013.01); *C07K 14/54* (2013.01); *C07K 14/65* (2013.01); *C07K 2319/02* (2013.01)

(58) Field of Classification Search
None
See application file for complete search history.

(56) References Cited

U.S. PATENT DOCUMENTS

| | | | |
|---|---|---|---|
| 6,605,286 B2 * | 8/2003 | Steidler | .................. A61P 35/00 514/18.9 |
| 10,406,184 B2 | 9/2019 | Kim et al. | |
| 10,765,623 B2 | 9/2020 | Kim et al. | |
| 2003/0202991 A1 | 10/2003 | Steidler et al. | |
| 2004/0235011 A1 * | 11/2004 | Cooper | .............. C12N 15/8509 435/69.7 |
| 2007/0117186 A1 | 5/2007 | Sahara et al. | |
| 2016/0222372 A1 | 8/2016 | Walper et al. | |
| 2016/0331686 A1 | 11/2016 | Polach et al. | |

FOREIGN PATENT DOCUMENTS

| | | |
|---|---|---|
| EP | 0128733 A1 | 12/1984 |
| EP | 1939218 A1 | 7/2008 |
| JP | 2000508162 A | 7/2000 |
| JP | 5354559 B2 | 11/2013 |
| KR | 1019990064308 A | 7/1999 |
| KR | 1020170015958 A | 2/2017 |
| KR | 1020170038462 A | 4/2017 |
| KR | 101802980 B1 | 12/2017 |
| KR | 20180003344 A | 1/2018 |
| WO | 9714806 A2 | 4/1997 |

(Continued)

OTHER PUBLICATIONS

Aldag et al., "Skin rejuvination using cosmetic products containing growth factors, cytokines, and matrikines: a review of the literature" 2016 Clinical, Cosmetic and Investigative Dermatology 4110419 (Year: 2016).*

(Continued)

*Primary Examiner* — Nancy J Leith
(74) *Attorney, Agent, or Firm* — CANTOR COLBURN LLP

(57) ABSTRACT

Provided are extracellular vesicles (EVs) derived from a recombinant microorganism including one or more polynucleotides encoding one or more target proteins, extracellular vesicles isolated from the microorganism, and a use of the extracellular vesicles.

15 Claims, 12 Drawing Sheets
Specification includes a Sequence Listing.

(56) References Cited

FOREIGN PATENT DOCUMENTS

WO    2015199441 A1    12/2015

OTHER PUBLICATIONS

Rodrigues et al., "Analysis of Yeast Extracellular Vesicles" Unconventional Protein Secretion: Methods and Protocols, Methods in Molecular Biology (Pompa and De Marchis (eds.), 175-190 (Year: 2016).*
Vargas et al., "Compositional and immunobiological analyses of extracellular vesicles released by Canddia albicans" 17(3) Cellular Microbiology 389-407 (Year: 2015).*
Peres da Silva et al., "Extracellular vesicle-mediated export of fungal RNA" 5 Scientific Reports 7763, 1-12 (Year: 2015).*
Kimn et al., "Yeast synthetic biology for hte production of recombinant therapeutic proteins" 15 FEMS Yeast Research 1-16 (Year: 2015).*
Oliveira et al., "Characterization of Yeast Extracellular Vesicles: Evidence for the Participation of Different Pathways of Cellular Traffic in Vescicle Biogeneisis" 5(6) PLoS ONE e11113, 1013 (Year: 2010).*
English Translation of Office Action dated Aug. 23, 2022, issued in corresponding CN Patent Application No. 201980030336.3, 8 pp.
Gurusamy Kutralam-Muniasamy, et al., Potential of yeast secretory vesicles in biodelivery systems, Drug Discovery Today, vol. 20, No. 6, Jun. 2015, pp. 659-664.
Office Action dated Aug. 23, 2022, issued in corresponding CN Patent Application No. 201980030336.3, 10 pp.
Behzadi, E. et al., 'The inhibitory impacts of Lactobacillus rhamnosus GG-derived extracellular vesicles on the growth of hepatic cancer cells', Microbial Pathogenesis, 2017, vol. 110, pp. 1-6.
Li, M. et al., 'Lactobacillus-derived extracellular vesicles enhance host immune responses against vancomycin-resistant enterococci', BMC Microbiology, 2017, vol. 17, Article 66, pp. 1-8.
International Search Report and Written Opinion mailed Aug. 1, 2019 in PCT/KR2019/005334.
1st Office Action issued Mar. 1, 2022 of JP Patent Application No. 2021-512349.
Extended European Search Report issued Mar. 28, 2022 of EP Patent Application No. 19796461.2.
Kunihiko Watanabe, "Functions and Biogenesis Mechanism of Membrane Vesicles Released by Bacteria, and Research Trend for Their Applications," chemical and biological activities, 2016, pp. 720-725, vol. 54(10).

* cited by examiner

1. PBS TREATMENT
2. TREATMENT WITH LMT1-21-DERIVED EV
3. TREATMENT WITH LMT1-21-DERIVED EV EXPRESSING IL-22

[Fig. 15]
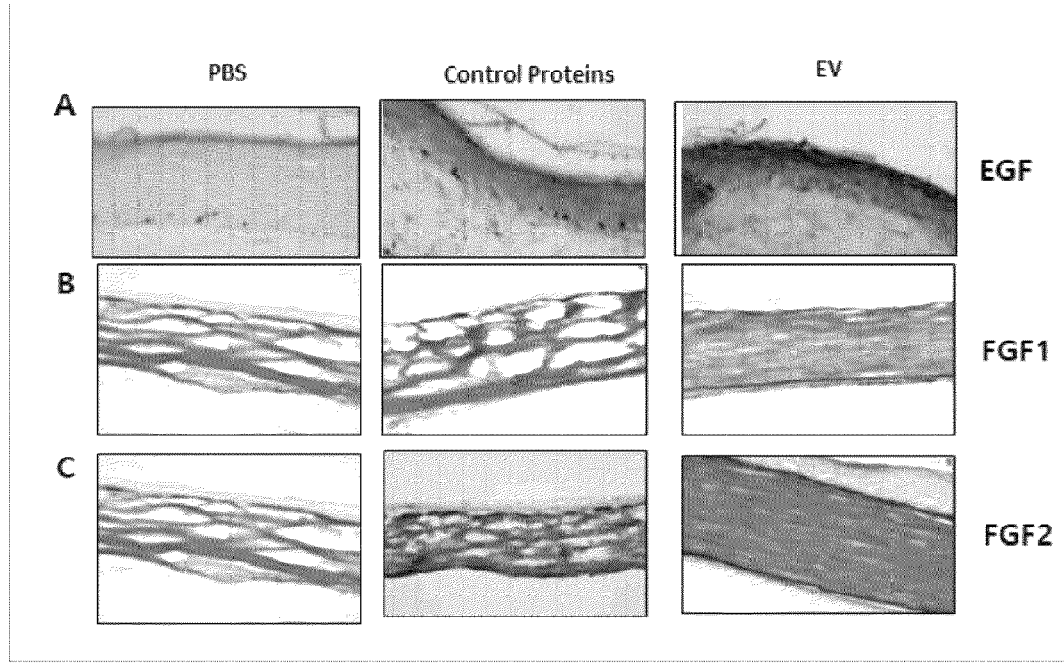
[Fig. 16]
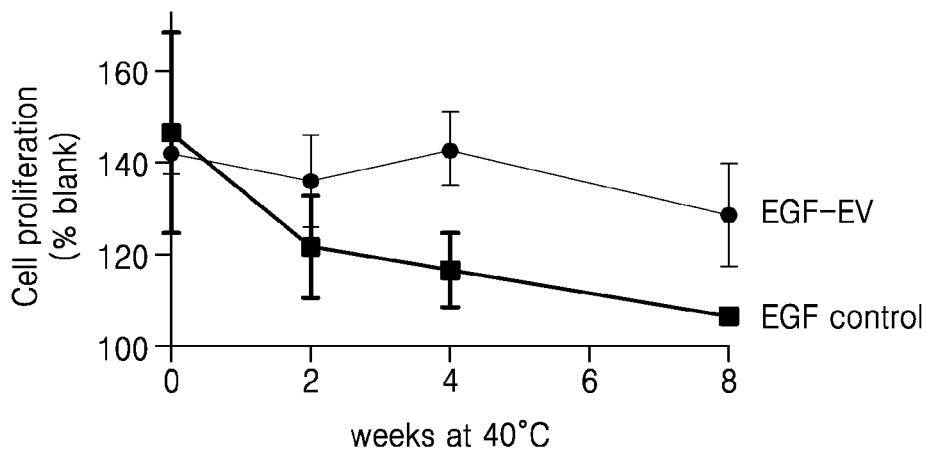
[Fig. 17]
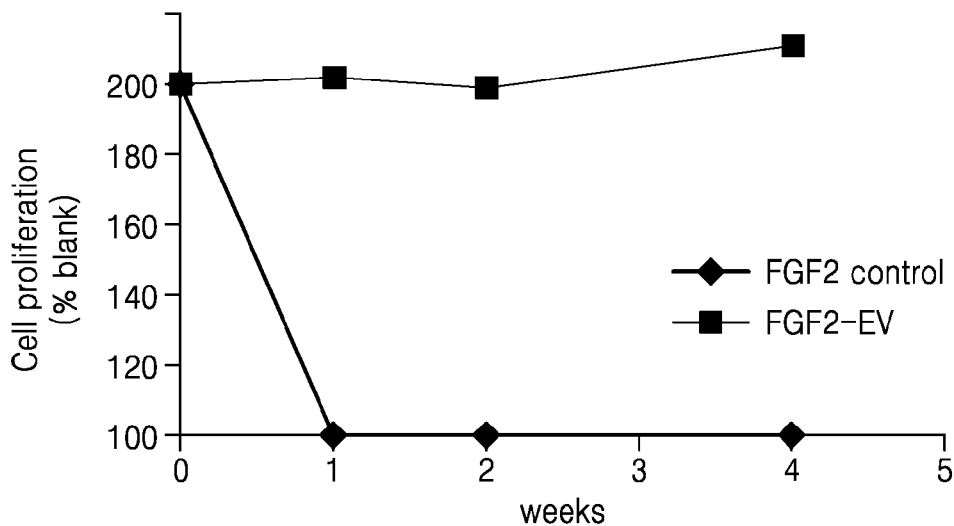

EXTRACELLULAR VESICLES DERIVED FROM RECOMBINANT MICROORGANISM INCLUDING POLYNUCLEOTIDE ENCODING TARGET PROTEIN AND USE THEREOF

CROSS-REFERENCE TO RELATED APPLICATIONS

This application is a national stage application of PCT/KR2019/005334 filed, May 3, 2019, which claims the benefit of Korean Patent Application No. 10-2018-0052157, filed on May 4, 2018, in the Korean Intellectual Property Office, the disclosure of each is incorporated herein in its entirety by reference.

TECHNICAL FIELD

Field

One or more embodiments relate to extracellular vesicles derived from a recombinant microorganism including a polynucleotide encoding a target protein, and a use thereof.

BACKGROUND ART

Most animal cells secrete extracellular vesicles (EVs) that have various sizes and components and originate from cells. Both prokaryotes and eukaryotes are known to secrete EVs.

EVs are membrane-structured vesicles having a size of about 20 nm to about 5 μm in diameter. EVs are heterogeneous in size and composition, and include a great number of different species such as exosomes (about 30 nm to about 100 nm), ectosomes, microvesicles (about 100 nm to about 1,000 nm), microparticles, outer membrane vesicles, and the like. The characteristics of EVs are affected by the characteristics of the origin cells.

Meanwhile, intracellular substances (for example, DNA, RNA, proteins, and the like) may be naturally loaded into EVs and extracellularly secreted. EVs have high biocompatibility due to having the same component as that of bio-membranes, and are as small as nano-sized, and thus have high mass transfer efficiency. Therefore, research is ongoing on delivery of drugs using EVs instead of using existing delivery systems such as liposomes, and the like. However, when a target protein is loaded into EVs, the efficiency of loading of the target protein into the EVs is low. Therefore, there is a need for a technique capable of stably loading a target protein into EVs with high efficiency.

DISCLOSURE OF INVENTION

Technical Problem

One or more embodiments include extracellular vesicles (EVs) derived from a recombinant microorganism including one or more polynucleotides encoding one or more target proteins, wherein the recombinant microorganism is a lactic acid bacterium or a yeast.

One or more embodiments include EVs isolated from the above-described recombinant microorganism.

One or more embodiments include a composition for delivering one or more target proteins to a subject, which includes EVs derived from the above-described recombinant microorganism as active ingredients and a carrier.

One or more embodiments include a method of treating a disease of a subject, including administering the composition to the subject.

One or more embodiments include a method of applying a cosmetic to a subject, including administering the composition to the subject.

One or more embodiments include a method of producing EVs, including: culturing the above-described microorganism to obtain a culture; and isolating EVs from the culture.

Additional aspects will be set forth in part in the description which follows and, in part, will be apparent from the description, or may be learned by practice of the presented embodiments.

Solution to Problem

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description.

An aspect of an embodiment provides extracellular vesicles (EVs) derived from a recombinant microorganism including one or more polynucleotides encoding one or more target proteins, wherein the recombinant microorganism is a lactic acid bacterium or a yeast.

The target protein may be linked to a signal peptide, i.e., it may be a fusion protein of a signal peptide and the target protein. The recombinant microorganism may load the target protein into extracellular vesicles (EVs) in an increased amount. In this case, the recombinant microorganism may have an increased EV-loading ability compared to a recombinant microorganism including one or more polynucleotides encoding one or more target proteins not having a signal peptide. The EV-loading ability refers to a degree to which the target protein is included in EVs or a degree to which the target protein is expressed in EVs. The EV-loading ability may refer to a loading ability compared to a parent microorganism not including a polynucleotide encoding a target protein.

The signal peptide may be encoded by the nucleotide sequence of SEQ ID NO: 4, or any one of the amino acid sequences of SEQ ID NOS: 21 to 60, or a sequence including or similar to the any one thereof.

In the recombinant microorganism, the lactic acid bacterium may belong to the genus selected from the group consisting of *Lactobacillus, Lactococcus*, and *Bifidobacterium*. The lactic acid bacterium may be *Lactobacillus paracasei, Lactobacillus brevis*, or *Lactobacillus plantarum*.

In the recombinant microorganism, the yeast may belong to the genus selected from the group consisting of *Saccharomyces, Pichia*, and *Hansenula*. The genus *Saccharomyces* may be *S. cerevisiae*. The genus *Pichia* may be *Pichia pastoris*, and the genus *Hansenula* may be *Hansenula polymorpha*.

In the recombinant microorganism, the target protein may be a growth factor, a cytokine, an antibody, an enzyme, an inhibitory protein, or a fragment thereof. The growth factor may be a fibroblast growth factor. The target protein may be selected from the group consisting of a fibroblast growth factor (FGF), an epidermal growth factor (EGF), a hepatocyte growth factor (HGF), an insulin-like growth factor (IGF), a placenta growth factor (PGF), a platelet-derived growth factor (PDGF), a transforming growth factor (TGF), a vascular endothelial growth factor (VEGF), thioredoxin (TRX), interleukin-1 (IL-1), IL-10, IL-22, IL-13, and a tumor necrosis factor (TNF). The target protein may be, for example, selected from the group consisting of IL-22, EGF, IGF1, FGF1 (hereinafter, also referred to as an acidic fibroblast growth factor (aFGF)), FGF2 (hereinafter, also referred to as a basic fibroblast growth factor (bFGF)), FGF7 (hereinafter, also referred to as a keratinocyte growth factor (KGF)), TGFa, and TRX.

In the recombinant microorganism, the signal peptide may be a signal peptide encoded by the nucleotide sequence of SEQ ID NO: 4, or any one of amino acid sequences of SEQ ID NOS: 21 to 60. A gene encoding the signal peptide may be linked such that the signal peptide is linked to the N-terminus of the target protein. The signal peptide may be naturally occurring or heterologous to the target protein. The target protein may be a heterologous protein to the recombinant microorganism. The recombinant microorganism may express the target protein. The target protein may be loaded into EVs in a state in which the signal peptide is cleaved. The target protein may be loaded on membranes of EVs or into EVs.

In the recombinant microorganism, the polynucleotide encoding a target protein may be expressible. The polynucleotide may be operably linked to a transcriptional control sequence. The transcriptional control sequence may be a promoter, an operator, an enhancer, or a terminator. The polynucleotide may be operably linked to a translational control sequence. The translational control sequence may be a ribosome binding site or a ribosome entry site sequence. The polynucleotide may be integrated into the genome of the microorganism or may be independently present. The polynucleotide may be included in a vector. The vector may be an expression vector. The vector may be a plasmid or a viral vector.

Another aspect of an embodiment provides EVs isolated from the above-described recombinant microorganism.

Another aspect of an embodiment provides a composition for delivering one or more target proteins to a subject, which includes extracellular vesicles derived from the above-described recombinant microorganism as active ingredients and a carrier.

In the embodiments regarding the recombinant microorganism and the composition, the EVs may be isolated from a culture broth of the microorganism. That is, the extracellular vesicles may be extracellularly secreted. The EVs may have an average diameter of about 20 nm to about 500 nm, for example, about 20 nm to about 200 nm or about 100 nm to about 200 nm. The EVs may include the target protein. The target protein may be located on membranes of the EVs or in the EVs.

The EVs may be isolated by any method capable of isolating EVs from a culture broth. For example, the EVs may be isolated by centrifugation, ultracentrifugation, filtration through a filter, ultrafiltration, gel filtration chromatography, ion exchange chromatography, precipitation, immunoprecipitation, pre-flow electrophoresis, capillary electrophoresis, or a combination thereof. The isolation method may include washing for removing impurities, concentration, and the like. The EVs may be produced using a method of separating the EVs, which will be described below. The EVs may be produced by ultrafiltration of the microorganism culture broth by using an ultrafiltration filter having a cutoff of 10 kD or more, for example, 50 kD or more, 100 kD or more, 300 kD or more, or 500 kD or more. The EVs may be precipitated by ultracentrifugation of the microorganism culture broth at 100,000×g or higher. The isolation may be performed using a method of producing EVs according to a seventh embodiment, which will be described below.

In the embodiment regarding the composition, the carrier may be physiologically acceptable, for example, pharmaceutically or cosmetically acceptable. The carrier may include saline, sterile water, Ringer's solution, buffer, cyclodextrin, a dextrose solution, a maltodextrin solution, glycerol, ethanol, liposomes, or a combination thereof, which are generally used. In addition, the carrier may include an antioxidant, a diluent, a dispersant, a surfactant, a binder, a lubricant, or a combination thereof.

The composition may be in a dosage form for oral or parenteral administration. The dosage form for parenteral administration may be a dosage form for topical administration. The dosage form for topical administration may be a dosage form for administration to the skin or the mucosa. The dosage form for parenteral administration may be a solution, a suspension, an emulsion, a dermatologic agent, a spray, or a puff.

The composition may be administered to a subject by skin application, mucosal application, nasal administration, or the like.

A suitable dose may vary depending on body weight, age, and gender of a patient, health conditions, diet, administration time, an administration method, excretion rate, the severity of a disease, and the like. A daily dose refers to an amount of an active ingredient sufficient to treat symptoms of a disease relieved by administering the composition to a subject in need of treatment. The dose may range from about 0.01 mg/day to 1,000 mg/day, or about 0.01 mg/day to about 500 mg/day, with respect to an adult with a body weight of 70 kg, and may be administered once to several times a day at predetermined time intervals.

The composition may be a cosmetic composition. The cosmetic composition may include ingredients commonly used in cosmetic compositions. The cosmetic composition may include general adjuvants such as an antioxidant, a stabilizer, a solubilizer, vitamins, a pigment, and a flavor, and carriers.

The cosmetic composition may be in the form of a solution, a suspension, an emulsion, a paste, a gel, a cream, a lotion, powder, oil, a powder foundation, an emulsion foundation, a wax foundation, or a spray. The cosmetic composition may be in the form of a nutritional cream, an astringent lotion, a soft lotion, a lotion, an essence, a nutritional gel, or a massage cream.

The composition may be used to promote the growth of fibroblasts or keratinocytes or collagen synthesis, in a subject. The composition may be used to prevent skin aging or alleviating wrinkles. In this case, the target protein may be a growth factor.

The composition may be delivered such that the target protein is topically delivered to the subject. The composition may be delivered transdermally, intradermally, orally, transmucosally, or intramucosally.

In the composition, the individual may be a mammal. The mammal may be a human, a dog, a cat, a horse, or a pig.

Another aspect of an embodiment provides a method of treating a disease of a subject, including administering the composition to a subject. The individual may be a mammal. The mammal may be a human, a dog, a cat, a horse, or a pig. The disease may be an inflammatory disease, wound, atopic dermatitis, psoriasis, or acne.

Another aspect of an embodiment provides a method of applying a cosmetic to a subject, including administering the composition to a subject. The administration may be performed by application to aged skin or wrinkled skin areas. The application of the cosmetic may be intended to alleviate aged skin or wrinkled skin.

Another aspect of an embodiment provides a method of producing EVs, including:

culturing the above-described recombinant microorganism to obtain a culture; and isolating EVs from the culture.

The culture may be incubation in a medium useful for the growth of the microorganism. The culture may be performed under conditions known to be suitable for lactic acid bacteria or yeast, for example, temperature and stirring conditions.

The isolation of the EVs from the culture may be performed using any method of isolating EVs from a culture.

The isolation may include: centrifuging the culture to obtain a supernatant; filtering the supernatant; and ultracentrifuging the filtrate to obtain a precipitate.

In the isolation, the centrifugation may be performed at about 1,000×g to about 20,000×g. In the filtration, the filtration may be filtration using an ultrafiltration filter. The filtration may be ultrafiltration of the supernatant using an ultrafiltration filter having a cutoff of 10 kD or more, for example, 50 kD or more, 100 kD or more, 300 kD or more, or 500 kD or more. In the ultracentrifugation of the filtrate to obtain a precipitate, the ultracentrifugation may be performed at 100,000×g or higher, for example, about 100,000×g to about 200,000×g.

The method may further include suspending the precipitate.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the disclosure as defined by the following claims.

BRIEF DESCRIPTION OF DRAWINGS

These and/or other aspects will become apparent and more readily appreciated from the following description of the embodiments, taken in conjunction with the accompanying drawings in which:

FIG. 15 illustrates results of observing the effect of growth factors which are contained in EVs or naked growth factors on the epidermal cell proliferation or collagenesis;

FIG. 16 illustrates result of stability test for EGFs which are contained in EVs or naked EGFs; and FIG. 17 illustrates result of stability test for FGF2s which are contained in EVs or naked FGF2s.

BEST MODE FOR CARRYING OUT THE INVENTION

Hereinafter, the present disclosure will be described in further detail with reference to the following examples. However, these examples are provided for illustrative purposes only and are not intended to limit the scope of the present disclosure.

EXAMPLE 1

Yeast Cell-Derived Extracellular Vesicles (EVs)

Recombinant yeast expressing a target protein was prepared and EVs were isolated from the yeast. Detailed procedures are as follows. Saccharomyces cerevisiae was used as the yeast cells.

1. Production of Expression Vector

Figure 1:
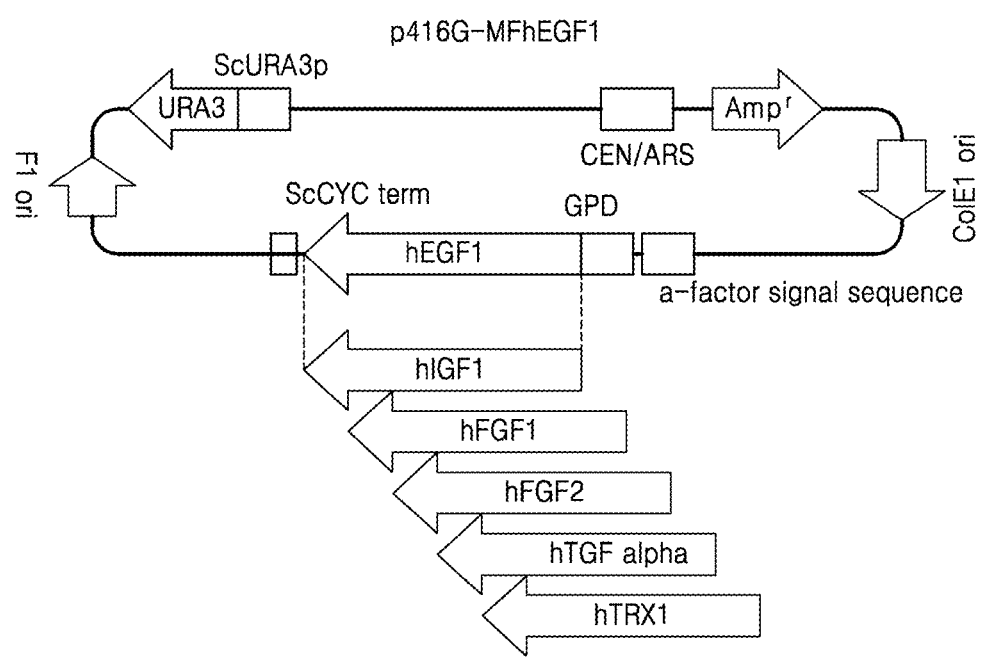
FIG. 1 illustrates an expression vector for expressing target proteins in yeast cells.

FIG. 1 illustrates an expression vector for expressing target proteins in yeast cells.

The expression vector was constructed using a sequence of plasmid pRS416 GPD (SEQ ID NO: 1), and the target proteins are hEGF1, hIGF1, hFGF1, hFGF2, hTGF alpha, and hTRX. The hEGF1, hIGF1, hFGF1, hFGF2, hTGF alpha, and hTRX proteins respectively have the amino acid sequences of SEQ ID NOS: 14, 15, 12, 13, 17, and 18, and these proteins may be encoded by the nucleotide sequences of SEQ ID NOS: 5, 6, 7, 8, 10, and 11, respectively. FGF7 may have the nucleotide sequence of SEQ ID NO: 9, and the amino acid sequence thereof may be the amino acid sequence encoded by the nucleotide sequence of SEQ ID NO: 9.

The vector of FIG. 1 was named p416G-MF-hEGF1 (IGF1, FGF1, FGF2, TGF alpha, and TRX) according to the target proteins.

First, codon-optimized target protein genes, i.e., human EGF1, IGF1, FGF1, FGF2, TGF alpha, and TRX genes, were synthesized according to the codon usage frequency of S. cerevisiae by MicroGene upon request. Each gene was constructed into the expression vector of FIG. 1 by using p416GPD vector (ATCC87360) (SEQ ID NO: 1). The expression vector of FIG. 1 includes a sequence in which a polynucleotide encoding a mating factor alpha-1 signal peptide (MF) (SEQ ID NO: 4) of S. cerevisiae is linked to upstream of the target protein gene. As a control, a gene to which a polynucleotide encoding a signal peptide (MF) (SEQ ID NO: 4) was not linked was used. In addition, a vector was constructed in the same manner as described above, except that p426GPD vector (ATCC 87361) (SEQ ID NO: 2) was used instead of the p416GPD vector (ATCC87360). The p416GPD vector is a vector present in cells with a low copy and the p426GPD vector is a vector present in cells with a high copy. In p416GPD and p426GPD, GPD represents the nucleotide sequence of the promoter GPD (SEQ ID NO: 3).

In FIG. 1, the vector includes a CEN/Ars sequence, which is the origin of replication of S. cerevisiae, an ampicillin resistance gene (Ampr) sequence, a ColE1 ori sequence, which is a sequence of the origin of replication of E. coli, a promoter GPD sequence, which is a promoter sequence of S. cerevisiae, a ScCYC term sequence, which is a CYC terminator sequence of S. cerevisiae, an F1 ori sequence, which is the origin of replication of bacteriophages, a promoter of S. cerevisiae, ORF, a terminator sequence (ScURA3p-URA3).

2. Expression of Target Protein in Yeast

Each of the p416G-MF-hEGF1 (IGF1, FGF1, FGF2, TGF alpha, and TRX) was transformed into a S. cerevisiae CEN. PK2-1 strain according to a LiCl method. The obtained transformed strain was primarily cultured for 1 day in 2 mL of a minimal uradrop out medium (6.7 g/L of yeast nitrogen base without amino acids (Sigma-Aldrich: Cat. No. Y0626), 1.92 g/L of yeast synthetic drop-out without uracil (Sigma-Aldrich: Cat. No. Y1501), and 2% (w/v) of glucose), and the cultured strain was inoculated into 15 mL of a minimal ura-drop out medium containing 1% of casamino acids at an initial $OD_{600}$ of 0.5, followed by main culture. The main culture was performed at 30° C. while stirring at 220 rpm for 2 days, and a sample group directly using a supernatant from which microbial bodies were removed was prepared. In addition, the supernatant was filtered using a 100 kDa cut-off membrane (Amicon Ultra-15 Centrifugal Filter Unit with Ultracel-10 membrane (100 K), Millipore: Cat. No. UFC910024) to obtain a concentrated filtrate, and the filtrate was ultracentrifuged at 150,000×g for 2 hours to isolate EVs and the EVs were suspended in 1 ml of PBS. At this time, western blotting was performed on the supernatant and the obtained EVs sample to confirm expression levels of the proteins.

Figure 2:
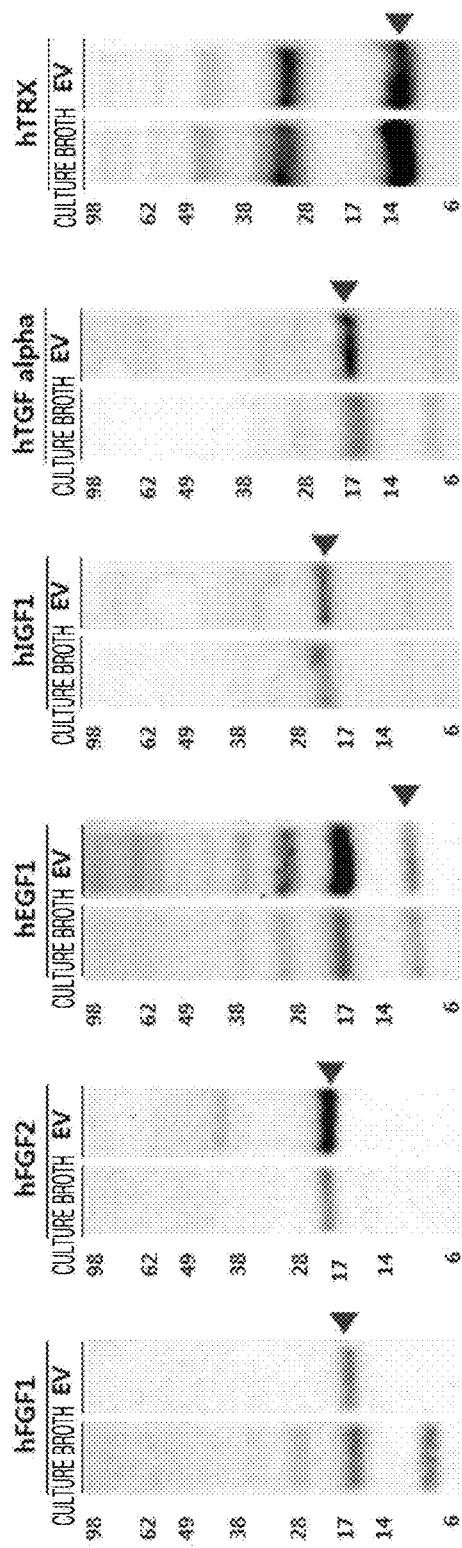
FIG. 2 illustrates levels of target proteins expressed in a supernatant and extracellular vesicles (EVs) derived from S. cerevisiae transformed with p416G-MF-hEGF1 (IGF1, FGF1, FGF2, TGF alpha, and TRX)

FIG. 2 illustrates levels of target proteins expressed in a supernatant and extracellular vesicles (EVs) isolated from S. cerevisiae transformed with p416G-MF-hEGF1 (IGF1, FGF1, FGF2, TGF alpha, and TRX). Lanes 1 and 2 are western blotting images showing an expression level of a fusion protein in which each target protein was linked to a signal peptide (MF). Lane 1 includes all proteins expressed in yeast cells and isolated from the culture broth, i.e., all target proteins loaded or not loaded in EVs. Lane 2 represents only the target proteins loaded in the EVs. As illustrated in FIG. 2, in the all six experimental groups, the respective target proteins are loaded in the EVs in significantly increased amounts.

Figure 3:
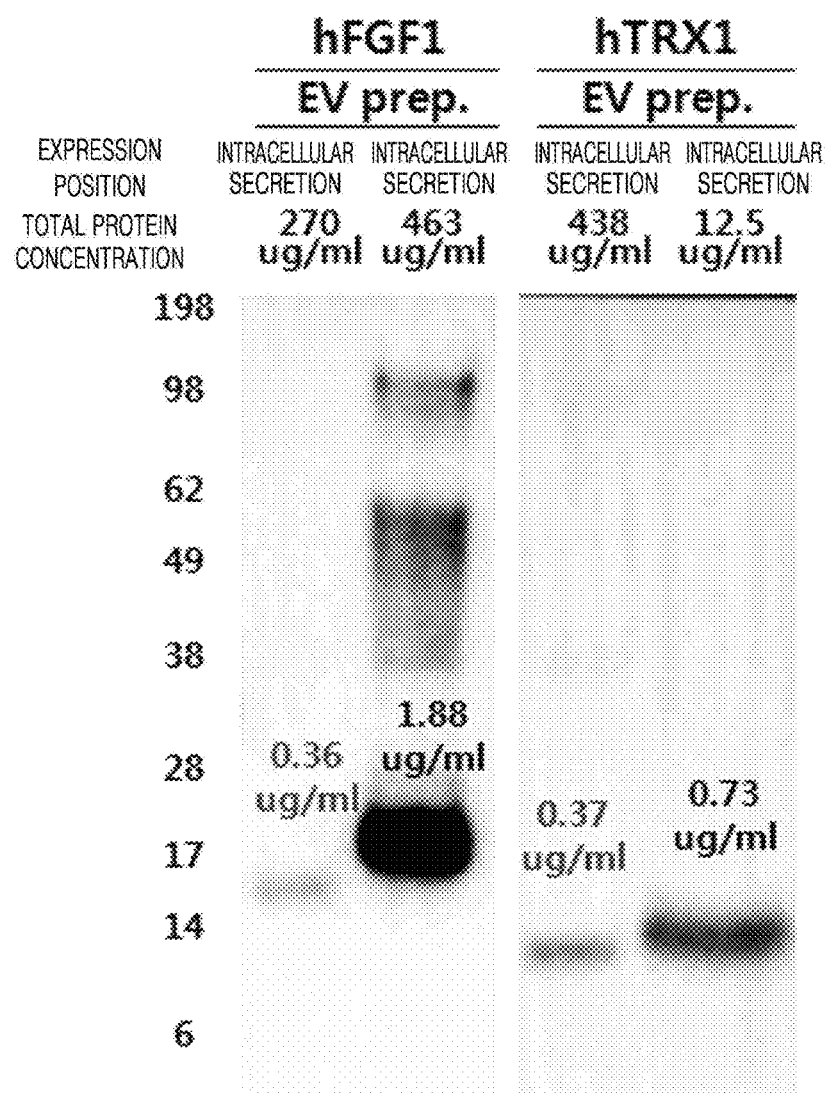
FIG. 3 illustrates levels of target proteins expressed in a supernatant and EVs derived from S. cerevisiae transformed with p416G-hFGF1, p416G-MF-hFGF1, p416G-hTRX and p416G-MF-hTRX.

FIG. 3 illustrates levels of target proteins expressed in a supernatant and EVs isolated from S. cerevisiae transformed with p416G-hFGF1, p416G-MF-hFGF1, p416G—hTRX and p416G-MF-hTRX. That is, FIG. 3 illustrates the degree of capturing by EVs according to the presence or absence of a signal peptide.

Lane 1 represents target proteins in EVs obtained from a culture broth of the strain expressed without a signal peptide, and lane 2 represents the expression of target proteins in EVs obtained from a culture broth of the strain expressed and secreted by a signal peptide. As illustrated in FIG. 3, the amounts of target proteins expressed in EVs when expressed and extracellularly secreted were significantly larger, i.e., 2.648 ng for FGF1 and 35.518 ng for TRX per 0.1 billion EVs, compared to the amounts of target proteins expressed intracellularly, i.e., 0.667 ng for FGF1 and 0.047 ng for TRX per 0.1 billion EVs.

3. Identification of Effect of Growth Factor-Containing EVs on Cell Proliferation The concentration of each target protein in the EVs isolated according to the method described in 2. above was measured, and then each target protein was sequentially diluted with PBS 10-fold each for 4 steps at a starting concentration of 20 μL. 20 μL of each diluent was added to a 96-well plate including an NIH3T3 cell line or HaCat cells at a density of 5,000 cells/well, followed by incubation at 37° C. for 48 hours. Subsequently, 10 μL of a cell counting kit-8 (Dojindo) solution was added to each well. After 2 hours, absorbance was measured at 450 nm. NIH3T3 cells were used for the cases of FGF1, FGF2, and IGF, and the HaCat cells were used for the cases of TGFa and EGF.

Figure 4:
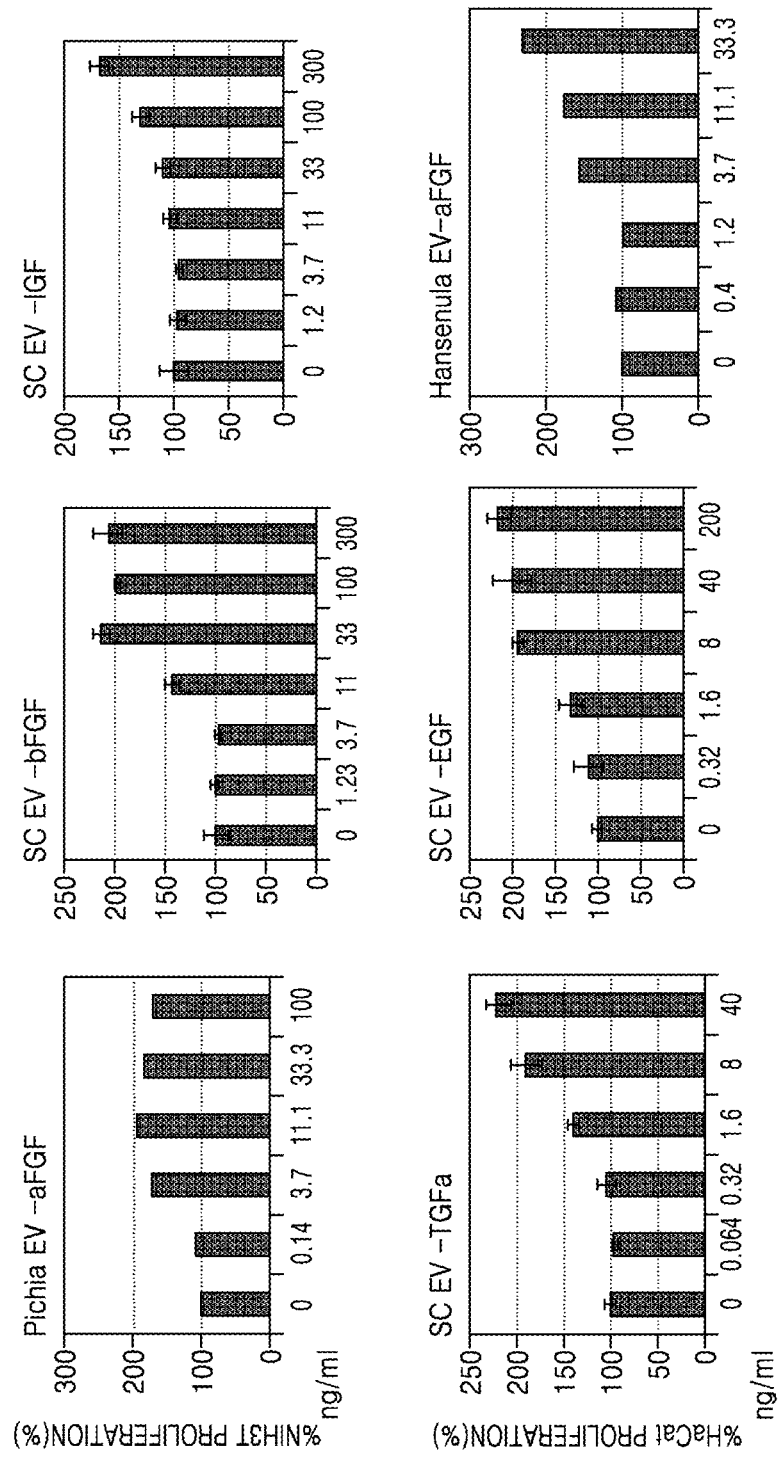
FIG. 4 illustrates an effect of growth factor-containing EVs derived from yeasts on cell proliferation.

FIG. 4 illustrates an effect of growth factor-containing EVs isolated from yeast on cell proliferation. In FIG. 4, SC denotes Saccharomyces cerevisiae.

As a result, the target protein-containing EVs increased the number of cells in a dose-dependent manner. In FIG. 4, Pichia EV-FGF1 and Hansenula EV-FGF1 were obtained by the same process as that used in the case of S. cerevisiae, except that Pichia pastoris or Hansenula polymorpha transformed with FGF1 was used. In FIG. 4, the horizontal axis denotes the concentration (w/v, ng/ml) of target protein in EVs in a medium. The vertical axis denotes a degree to which cells were proliferated in an EV-containing solution by comparison with a control (100%), wherein the degree was expressed as a percentage.

4. Identification of IL-22 Expression

The expression vector p426G-MF-IL-22 was constructed using IL-22 as a target protein in the same manner as described in 1. above, and as described in 2. above, the expression vector was transformed into the S. cerevisiae CEN.PK2-1. As a control, the same p426G-MF vector but not including IL-22 was used.

In particular, a Colo205 cell line was cultured in a 96-well plate in RPMI medium for 48 hours at 37° C., and then transformed with the p426G-MF-IL22 vector or the p426G-MF vector to purify EVs derived from yeast expressing or not expressing IL22. The EVs was suspended in PBS at a concentration of 0.5 mg/mL, and 20 μL of the EVs was added to each well of the 96-well plate, followed by further culturing for 6 hours at 37° C. Thereafter, proteins were extracted from the cell line to compare expression levels of IL-22 indirectly through the expression level of IL-10. IL-22 has the amino acid sequence of SEQ ID NO: 19. IL-22 is known to promote the production of IL-10.

Figure 5:
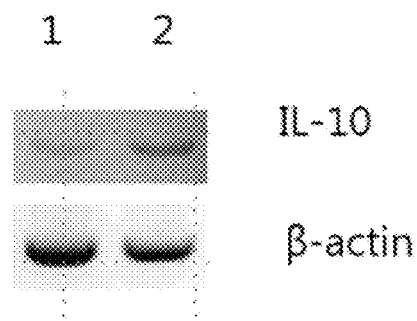
FIG. 5 illustrates the production of IL-10 in cells treated with S. cerevisiae derived IL-22-containing EVs or IL-22-free EVs.

FIG. 5 illustrates the production of the IL-10 protein identified from among proteins extracted from the Colo205 cell line treated with IL-22-containing EVs or IL-22-free EVs. As illustrated in FIG. 5, when the cells were cultured after being brought into contact with the IL-22-containing EVs, the production of the IL-10 protein was significantly increased compared to that in the IL-22-free EVs. In FIG. 5, lane 1 represents the degree of production of the IL-10 protein of the Colo205 cell line treated with the IL-22-free EVs, and lane 2 represents the degree of production of the IL-10 protein of the Colo205 cell line treated with the IL-22-containing EVs.

5. Fusion of Yeast-Derived EVs with Cells

EVs were isolated from an untransformed *S. cerevisiae* CEN.PK2-1 strain as described above. 1 ml of the isolated EVs (0.5 mg/ml PBS) was placed in a 5 μM 5-carboxyfluorescein N-hydroxysuccinimidyl ester (CFSE) solution at room temperature for 30 minutes. Subsequently, the remaining CFSE was removed from the solution by using a PD-10 desalting column (GE) to obtain CFSE-labeled EVs. An NIH3T3 cell line was cultured in 0.2 mL RPMI medium in each well of a 96-well plate for 48 hours at 37° C., and then 10 μL (red) or 20 μL (green) of the CFSE-labeled EVs in PBS was added to each well, followed by further culturing for 24 hours at 37° C. Thereafter, the cells were washed with PBS. The residual cells were allowed to pass through a flow cytometer and fluorescence therefor was measured. As a control, 0.5 μg/ml of BSA was labeled with CFSE and 20 μL of the resulting material was used.

Figure 6:
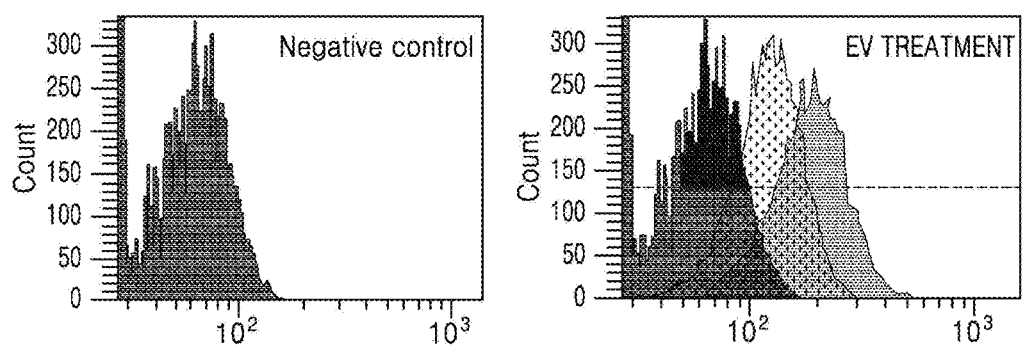
FIG. 6 illustrates results of observing the degree of binding of S. cerevisiae derived EVs labeled by CFSE-labeled EVs with cells through cell flow analysis.

FIG. 6 illustrates results of observing the degree of fusion between CFSE-labeled EVs and cells through cell flow analysis. In FIG. 6, negative control (left graph) represents cells brought into contact with the CFSE-labeled BSA, and experimental group (right graph) represents observation results of cells brought into contact with 10 μL (red) or 20 μL (green) of the CFSE-labeled EVs. As a result, as illustrated in the right graph of FIG. 6, cells were stained with CFSE, from which it was confirmed that the EVs were fused with the cells, resulting in introduction of components of the EVs into the cells. NIH3T3 cells are a standard fibroblast cell line.

6. Confirmation of Skin Toxicity of Yeast-Derived EVs

The toxicity of yeast-derived EVs to the skin was measured through toxicity experiments for artificial skin in accordance with the OECD guidelines. As artificial skin, Neoderm™-ED (manufactured by Taigo Science Co., Ltd.) was used.

EVs derived from *S. cerevisiae*, *Pichia pastoris*, or *Hansenula polymorpha* were isolated. The *S. cerevisiae*-derived EVs were isolated as described in 2. above. The isolation of the *Pichia pastoris*- or *Hansenula polymorpha*-derived EVs was performed in the same manner as in 2. above, except that *Pichia pastoris* and *Hansenula polymorpha* were used for the respective cases.

30 μL of each of the isolated EVs, PBS as a negative control, and 5% SDS as a positive control were applied to the Neoderm™-ED artificial skin, followed by incubation for 15 minutes at 37° C. Subsequently, the artificial skin was washed with PBS, and then immersed in 2 ml of an assay medium (Taigo Science Co., Ltd.) in a 12-well plate, followed by further incubation for 42 hours at 37° C.

The incubated artificial skin was taken out and transferred to a 0.3% MTT solution (0.3 mg/ml), followed by incubation for 3 hours at 37° C. Thereafter, the artificial skin was taken out again, each tissue was separated using an 8 mm biopsy punch, added to 500 μl of 0.04N HCl-isopropanol, and then decolored for 4 hours. Absorbance at 570 nm was measured, and then compared with that of the controls to obtain viability (%).

As a result, a case in which the measured viability was a median between values of the positive and negative controls or greater was determined as non-toxic. The viability was calculated according to Equation below:

Viability=absorbance of test material/absorbance of negative control×100

Figure 7:
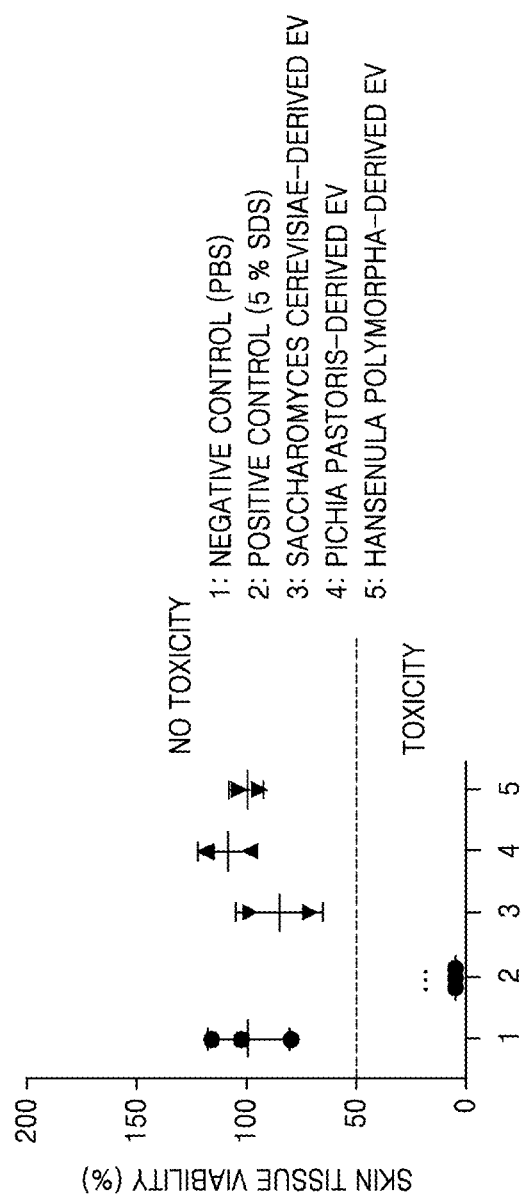
FIG. 7 illustrates results of measuring toxicity of yeast-derived EVs to the skin.

FIG. 7 illustrates results of measuring the toxicity of yeast-derived EVs to the skin.

In FIG. 7, 1: negative control (PBS), 2: positive control (5% SDS), 3: *S. cerevisiae*derived EVs, 4: *P. pastoris*-derived EVs, 5: *H. polymorpha*-derived EVs.

EXAMPLE 2

Lactic Acid Bacteria (LAB) Cell-Derived EVs

Recombinant lactic acid bacteria expressing target proteins were prepared and EVs were isolated from the lactic acid bacteria. Detailed procedures are as follows. As LAB cells, *Lactobacillus paracasei* LMT1-21 (KCTC13422BP), *Lactobacillus brevis* LMT1-46 (KCTC13423BP) and/or *Lactobacillus plantarum* LMT1-9 (KCTC13421BP) were used.

1. Construction of Gene Expression Vector

For a target gene, a nucleotide sequence having a codon optimized for LAB used was obtained from amino acid sequences of a protein using the codon optimization tool (http://sq.idtdna.com/CodonOpt), a sequence having recognition sequences of BamHI and XhoI restriction enzymes at opposite terminals thereof was devised, and DNA having this sequence was synthesized (Macrogen, Korea). The synthesized gene was digested with the BamHI and XhoI restriction enzymes. In addition, the parent vector pMT182-PR4 (SEQ ID NO: 20) was digested with the same restriction enzymes and purified using a gel purification kit and then dephosphorylated using alkaline phosphatase (AP). This parental vector includes a promoter PR4 to express the target protein and the signal peptide SP4 (SEQ ID NO: 21) to extracellulary secrete it.

1 μL of the prepared vector DNA, 3 μL of insert DNA, 0.5 μL of T4 DNA ligase (Takara, Japan), and 1 μL of a buffer solution were added to 5.5 μL of distilled water a total volume of 10 μL. The reaction solution was incubated at 16° C. for 12 hours to allow a ligation reaction, and the resulting ligated product was transformed into an *E. coli* Top10 strain according to a method (Sambrook et al., Molecular Cloning: A laboratory manual, 2nd ed.1989). The sequence of the plasmid obtained from each colony was analyzed and identified. The target proteins used were FGF1, FGF2, EGF, IGF, KGF, TGFa, TRX, and IL-22. These target proteins respectively have the amino acid sequences of SEQ ID NOS: 1, 2, 3, 4, 5, 6, 7, and 8.

2. LAB transformation

The obtained cloned DNA was transformed into three kinds of lactic acid bacteria.

Each strain was cultured in 50 mL of MRS until $OD_{600}$ reached 0.5, and then centrifuged at 7,000 rpm for 10 min at 4° C. and washed twice with 25 mL of ice-cold EPS (containing 1 mM $K_2HPO_4$ $KH_2PO_4$, pH 7.4, 1 mM $MgCl_2$, and 0.5 M sucrose). These cells were suspended in 1 mL of ice-cold EPS to prepare competent cells to be used for electroporation, and stored in a deep freezer at −80° C. 40 μL of the competent cells and 1 μg/μL of vector DNA were transferred to a cuvette and left on ice for 5 minutes. After pulsing at 25 μF, 8 kV/cm, and 400 ohms, 1 mL MRS liquid medium was added immediately and incubated at 37° C. for about 1 hour. The cells were plated on MRS medium containing 10 μg/ml of chloramphenicol and cultured at 37° C. for 49 hours to obtain transformed cells.

3. Isolation of EVs

Among the resulting transformed LAB strains, the KCTC13422BP strain was statically cultured in an MRS liquid medium at 37° C. for 16 hours, and then 2% (w/v) of the strain was inoculated again into the MRS liquid medium, followed by static culture for 16 hours. The obtained culture was centrifuged at 5,000×g for 15 minutes to obtain a supernatant from which LAB was removed, and then concentrated 20-fold by ultrafiltration using a 100 kDa molecular weight cut-off (MWCO) ultrafiltration membrane. The concentrate was ultracentrifuged at 150,000×g for 3 hours to obtain a sunken pellet, and the pellet was resuspended in PBS to obtain an EV solution. The size and number of the obtained EVs were measured using NanoSight NS300 (Malvern). The results thereof are illustrated in FIG. 8.

Figure 8:
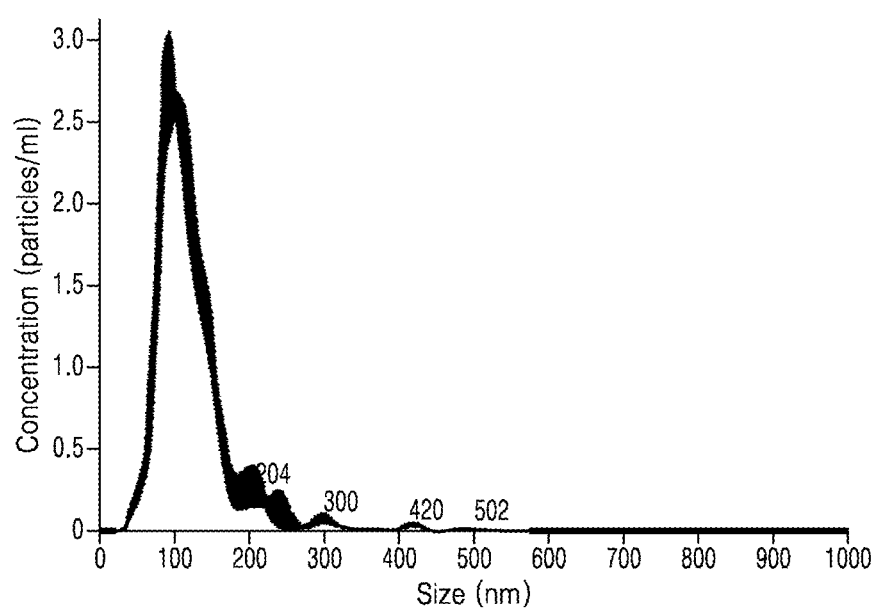
FIG. 8 illustrates the size and concentration distribution of EVs derived from transformed lactic acid bacteria.

FIG. 8 illustrates the size and concentration distribution of EVs isolated from transformed LAB. In FIG. 8, the horizontal axis denotes a diameter, and the vertical axis denotes a concentration (particles/ml). In FIG. 8, the used LAB was a KCTC13422BP strain, and the target protein was FGF1.

As illustrated in FIG. 8, EVs were distributed such that 90% of particles were distributed at the particle sizes of 80 nm to 250 nm.

4. Confirmation of Presence of Target Protein In EVs

Western blotting was performed on the EV solution obtained in 3. above to confirm whether the target proteins were present in the EVs. The EVs were isolated from the KCTC13422BP strain (hereinafter, also referred to as LMT1-21) transformed with a vector obtained by cloning pMT182-PR4 with a gene encoding FGF1 or TRX. At this time, the gene used has a sequence fused or not fused with a signal peptide, i.e., an SP4 sequence.

Western blotting was performed as follows. A 4× loading buffer (thermo) and a 10× reducing agent (thermo) were added to 5 µL of the EV solution, and then electrophoresed on a sodium dodecyl sulfate-polyacrylamide gel electrophoresis (SDS-PAGE) gel. Proteins of this gel were transferred to a nitrocellulose membrane, which was then blocked by incubation in Tris-buffered saline with Tween 20 (TBST) containing 5% skim milk as a blocking solution for 2 hours. After washing with TBST three times for 5 minutes, the membrane and primary antibodies were added to the blocking solution and incubated for 2 hours to induce antigen-antibody binding. After washing with TBST, secondary antibodies were added thereto. After standing for 1 hour, the amounts and positions of the target proteins were confirmed using an enhanced electrochemical (ECL) system.

Figure 9:
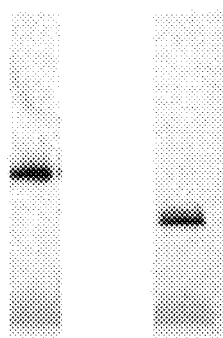
FIG. 9 illustrates western blotting results of EV solutions.

FIG. 9 illustrates western blotting results of the EV solution. As illustrated in FIG. 9, FGF1 and TRX are expressed in EVs isolated from LMT1-21 transformed with a vector obtained by cloning pMT182-PR4 with FGF1 and TRX fused with a signal peptide, respectively, from which it is evident that these target proteins are present in EVs.

Figure 10:
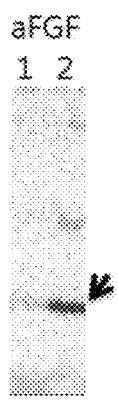
FIG. 10 illustrates western blotting results of EVs derived from LMT1-21 transformed with recombinant pMT172 including a gene encoding FGF1 that was fused or not fused with a signal peptide gene.

FIG. 10 illustrates western blotting results of EVs isolated from LMT1-21 transformed with a recombinant vector including a gene encoding FGF1 that was fused or not fused with a signal peptide gene, i.e., pMT182-PR4-FGF1 or pMT182-PR4-SP4-FGF1. In FIG. 10, lane 1 represents EVs when the FGF1 gene was expressed in the absence of a signal peptide, and lane 2 represents EVs when a gene encoding a fusion protein of a signal peptide and FGF1 was expressed.

5. Identification of Efficacy of EVs Containing Growth Factor Derived from LAB on Cell Proliferation The EVs isolated from the 1 L LAB culture broth were suspended in 1 ml of PBS according to the method described in 3, above. An NIH3T3 cell line (or HaCat cells) in DMEM medium was seeded into each well of a 96-well plate at a density of 5,000 cells/well and cultured at 37° C. for 48 hours. Then, 20 µL of the solution including EVs expressing a growth factor or PBS as a control was added thereto. The cells were cultured under the same conditions for 48 hours, and then 10 µL of a cell counting kit-8 (Dojindo) solution was added to each well. After 2 hours, absorbance was measured at 450 nm. NIH3T3 cells were used for the cases of FGF1, FGF2, and IGF, and HaCat cells were used for the cases of KGF, TGFa, and EGF.

Figure 11:
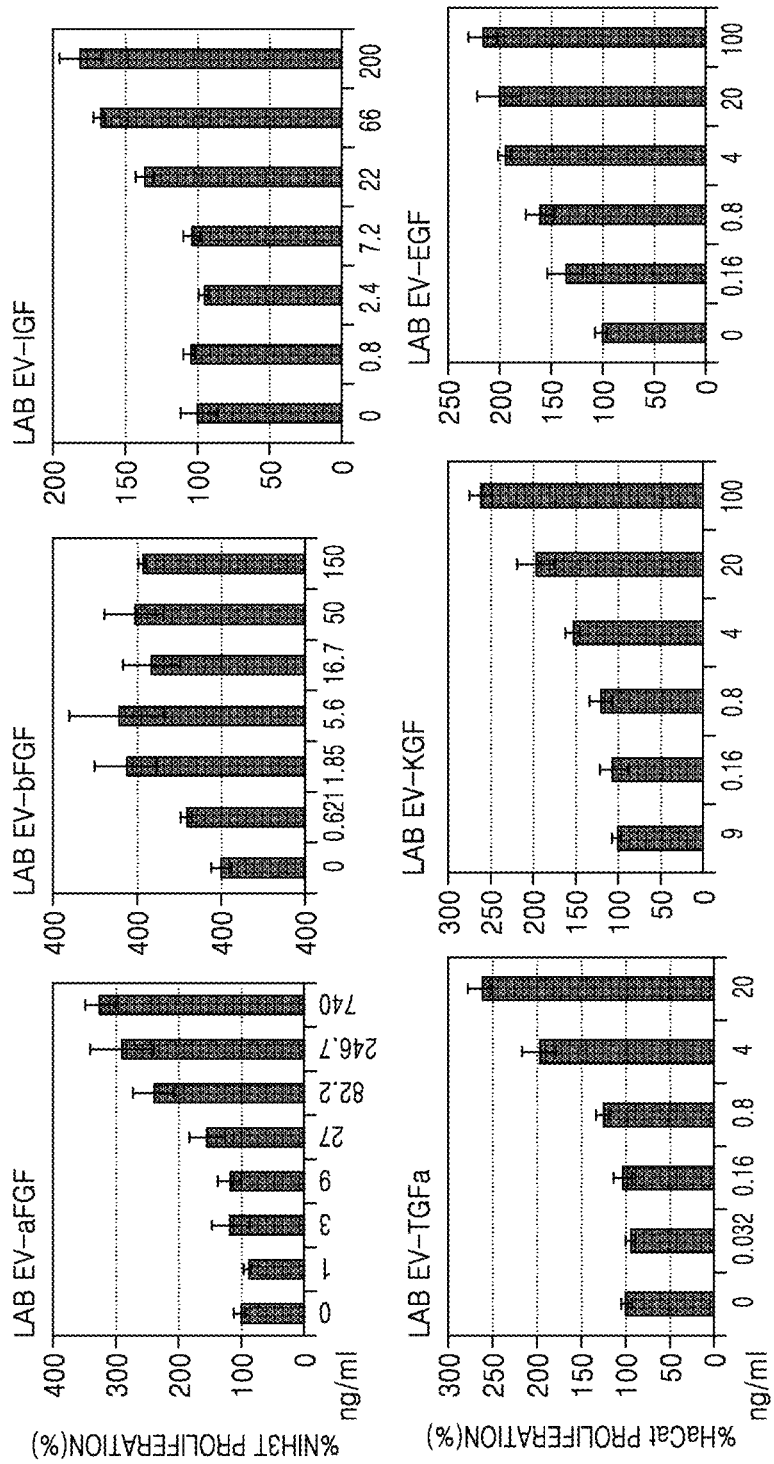
FIG. 11 illustrates an effect of growth factor-containing EVs derived from lactic acid bacteria on cell proliferation.

FIG. 11 illustrates an effect of growth factor-containing EVs isolated from LAB on cell proliferation. In FIG. 11, LAB denotes a lactic acid bacterium (KCTC13422BP strain). As a result, the target protein-containing EVs increased cell concentration in a dose-dependent manner. In FIG. 11, the horizontal axis denotes the concentration (w/v) of a target protein included in the EVs. The vertical axis denotes a degree of cell proliferation by the EV-containing solution used by comparison with a control, wherein the degree is expressed as a percentage.

6. Efficacy of Growth Factor-Containing EVs: Confirmation of IL-10 Expression A vector expressing IL-22 was constructed according to 1. and 2. above, and this vector was transformed into LMT1-21. EVs were isolated from LMT1-21 transformed with the vector expressing IL-22 according to 3. above. To confirm whether the EVs promote IL-10 expression in the cells, the presence of IL-22 was indirectly assumed.

In particular, a Colo205 cell line was cultured in RPMI medium in a 96-well plate for 48 hours at 37° C., EVs derived from LAB expressing or not expressing IL-22 were isolated and suspended in PBS at a concentration of 0.5 mg/mL, and then 20 µL of each suspension was added to each well, followed by further culturing for 6 hours at 37° C. Subsequently, proteins were extracted from the cell line, i.e., by cell lysis to obtain a lysate, and among the proteins, expression levels of IL-10 were compared with each other.

Figure 12:
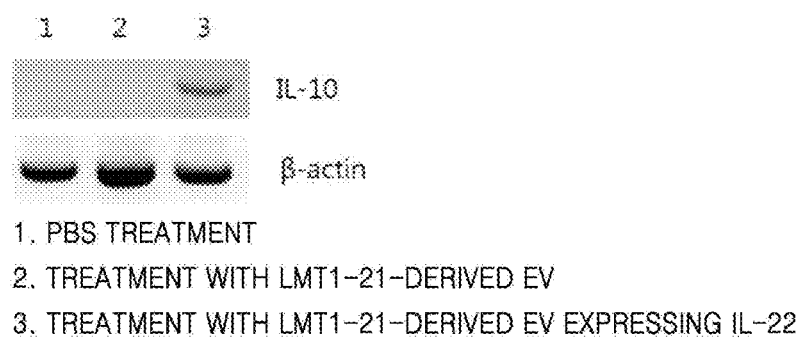
FIG. 12 illustrates production of IL-10 in cells treated with IL-22-containing EVs derived from LMT1-21 or IL-22-free EVs.

FIG. 12 is a set of images showing western blotting results of proteins derived from cells that were brought into contact with LMT1-21-derived EVs. In FIG. 12, lane 1 represents PBS, lane 2 represents LMT1-21-derived EVs, and lane 3 represents EVs derived from LMT1-21 expressing IL-22.

7. Fusion of LAB-Derived EVs with Cells

EVs were isolated from an untransformed LAB strain (KCTC13422BP) as described above. 1 ml of the isolated EVs (0.5 mg/ml PBS) was placed in a 5 µM CFSE solution at room temperature for 30 minutes. Subsequently, the remaining CFSE was removed from the solution by using a PD-10 desalting column (GE) to obtain CFSE-labeled EVs. An NIH3T3 cell line was cultured in 0.2 mL RPMI medium in each well of a 96-well plate for 48 hours, and then 10 µL (red) or 20 µL (green) of the CFSE-labeled EVs in PBS was added to each well, followed by further culturing for 24 hours. Thereafter, the cells were washed with PBS. The residual cells were allowed to pass through a flow cytometer and fluorescence therefor was measured. As a control, 0.5 µg/ml of BSA was labeled with CFSE and 20 µl of the resulting material was used.

Figure 13:
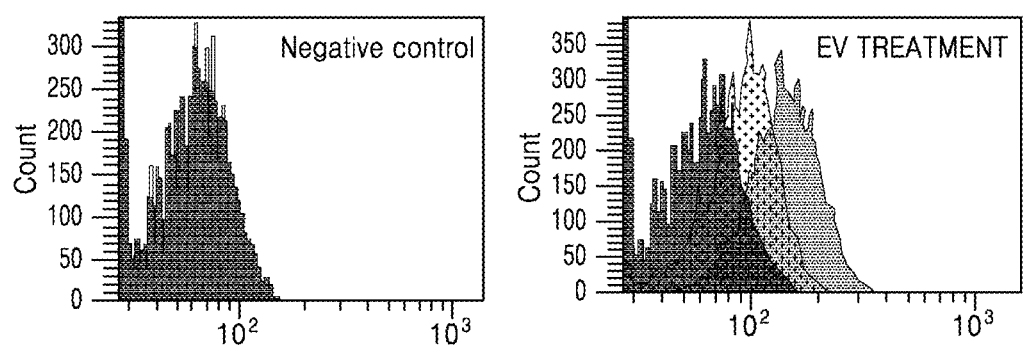
FIG. 13 illustrates results of observing the degree of fusion of CFSE-labeled EVs with cells through cell flow analysis.

FIG. 13 illustrates results of observing the degree of fusion of CFSE-labeled EVs with cells through cell flow analysis. In FIG. 13, negative control (left graph) represents cells brought into contact with the CFSE-labeled BSA, and experimental group (right graph) represents observation results of cells brought into contact with 10 µL (red) or 20 µL (green) of the CFSE-labeled EVs. As a result, as illustrated in the right graph of FIG. 13, cells were stained with CFSE, from which it was confirmed that the EVs were fused with the cells, resulting in introduction of components of the EVs into the cells. NIH3T3 cells are a standard fibroblast cell line.

8. Confirmation of Skin Toxicity of LAB-Derived EVs

The toxicity of LAB-derived EVs to the skin was measured through toxicity experiments for artificial skin in accordance with the OECD guidelines. As artificial skin, Neoderm™-ED (manufactured by Taigo Science Co., Ltd.) was used.

EVs derived from LMT1-21, LMT1-9, or LMT1-46 were isolated. These EVs were isolated as described in 2. above. 30 µL of each of the isolated EVs, PBS as a negative control, and 5% SDS as a positive control were applied to the Neoderm™-ED artificial skin, followed by incubation for 15 minutes at 37° C. Subsequently, the artificial skin was washed with PBS, and then immersed in 2 ml of an assay medium (Taigo Science Co., Ltd.) in a 12-well plate, followed by further incubation for 42 hours at 37° C.

The incubated artificial skin was taken out and transferred to a 0.3% MTT solution (0.3 mg/ml), followed by incubation for 3 hours. Thereafter, the artificial skin was taken out again, each tissue was separated using an 8 mm biopsy punch, added to 500 µl of 0.04N HCl-isopropanol, and then decolored for 4 hours. Absorbance at 570 nm was measured, and then compared with that of the controls to obtain viability (%). As a result, a case in which the measured viability was a median between values of the positive and negative controls or greater was determined as non-toxic. The viability was calculated according to Equation below:

Viability=absorbance of test material/absorbance of negative control×100

Figure 14:
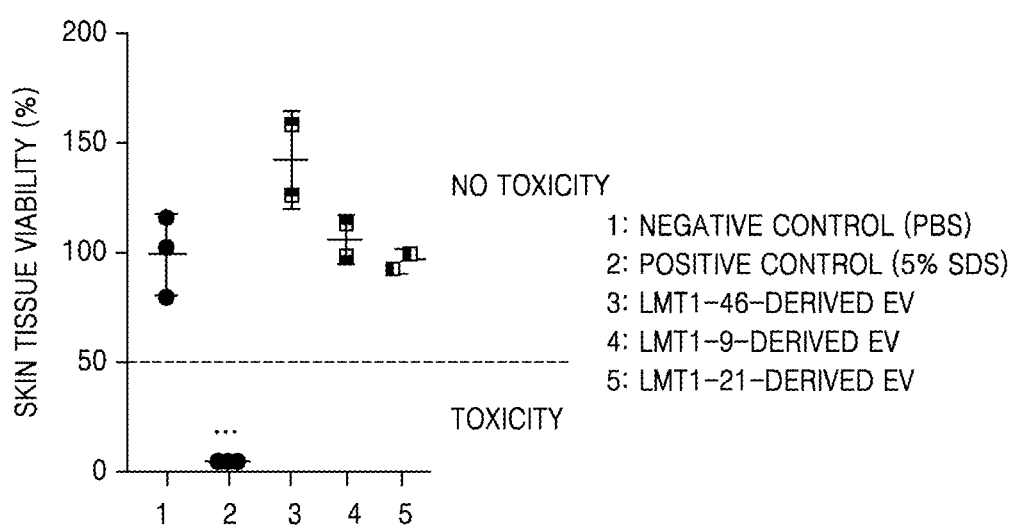
FIG. 14 illustrates results of measuring the toxicity of yeast-derived EVs to the skin.

FIG. 14 illustrates results of measuring toxicity of LAB-derived EVs to the skin. In FIG. 14, 1: negative control (PBS), 2: positive control (5% SDS), 3: LMT1-46-derived EVs, 4: LMT1-9-derived EVs, and 5: LMT1-21-derived EVs.

EXAMPLE 3

Comparing the Cell Proliferation Effect of Growth Factor-Containing EVs with that of Naked Growth Factors 1. Preparation of Growth Factor-Containing EVs Growth factor-containing EVs were isolated from *Pichia pastoris* transformed with p416G-MF-EGF, p416G-MF-FGF1 and p416G-MF-FGF2, respectively as the same manner with item 3 in Example 1. Each of those was suspended in PBS to adjust the concentration of EGF to 10 ug/ml and the concentration of FGF1 or FGF2 to 1 ug/ml. As control, naked EGF, FGF1, and FGF2 proteins were purchased from AbCam, and suspended in PBS to the same concentrations above.

2. Comparing the Effect of Growth Factor-Containing EVs with that of Naked Growth Factors on Cell Proliferation Artificial skin, Neoderm™-ED was purchased from Taigo Science Co., Ltd. The artificial skins were washed with PBS, and then added to 2 mL PBS, 2 mL EV-growth factor-containing solutions as prepared above and 2 mL of control solution containing naked EGF, FGF1, or FGF2 protein as prepared above in wells of a 12-well plate, followed by further incubation for 24 hours at 37° C. After washing with PBS three times, artificial skins were fixed in 4% paraformaldehyde solution (Sigma, USA) for 18 hours at 37° C. and frozen-sectioned using Leica Biosystems. Immunohistochemistry (IHC) was performed using anti-Ki-67 antibody (AbCam) for EGF-EV and control protein, and anti-collagen antibody (AbCam) for FGF1-EV, FGF2-EV and control proteins, followed by addition of DAB (3,3'Diaminobenzidine). The results were photographed under a microscope. In general, abundance of Ki-67 or collagen is observed with brown color. Ki-67 is known as a biomarker of epidermal cell proliferation.

As seen in FIG. 15, better epidermal cell proliferation was observed with EGF-EV treatment compared with the PBS and the control protein treatment (Row A). Also, better collagen synthesis was observed when using FGF1-EV and FGF2-EV compared with the using PBS or the control proteins (Row B and C). According to these results, growth factors which were contained in EVs were more effective on cell proliferation compared with naked growth factors regardless of growth factor types, and among them, FGF2-EV was most effective compared with any other growth factors which were contained in EVs or not contained in EVs.

EXAMPLE 4

Comparing the Growth Factor Stability

1. EGF-EV Stability compared with naked EGF Stability

*Pichia pastoris* derived EGF-EV and the control protein, i.e., EGF protein which is not contained in EV were prepared as the same manner as described in item 2 in Example 1. Briefly, the EGF-EVs or the EGF protein was suspended in 1 ml of PBS to concentration of to be 10 ug/ml. and then incubated at 40° C. for 8 weeks. Biweekly the samples were aliquoted and diluted using PBS to the concentration of 100 ng/ml for cell proliferation activity assay.

HaCat cells in DMEM medium was seeded into each well of a 96-well plate at a density of 5,000 cells/well and cultured at 37° C. for 48 hours. Then, 20 µL of the above each sample of EGF-EV, control protein, and PBS was added thereto. The cells were cultured under the same conditions for 48 hours, and then 10 µL of a cell counting kit-8 (Dojindo) solution was added to each well. After 2 hours, absorbance was measured at 450 nm.

As seen in FIG. 16, EGFs which contained in EVs were more stable then naked EGFs.

2. FGF2-EV Stability Compared with Naked FGF2 Stability

*Pichia pastoris* derived FGF2-EV and the control protein, i.e., FGF2 protein which is not contained in EV were prepared as the same manner as described in item 2 in Example 1. Briefly, the FGF2-EVs or the FGF2 protein was suspended in 1 ml of PBS to concentration of to be 10 ug/ml. and then incubated at room temperature for 4 weeks. Each sample was aliquoted and diluted using PBS on regular basis to the concentration of 100 ng/ml for cell proliferation activity assay.

NIH3T3 cells in DMEM medium was seeded into each well of a 96-well plate at a density of 5,000 cells/well and cultured at 37° C. for 48 hours. Then, 20 µL of the above each sample of FGF2-EV, control protein, and PBS was added. The cells were cultured under the same conditions for 48 hours, and then 10 µL of a cell counting kit-8 (Dojindo) solution was added to each well. After 2 hours, absorbance was measured at 450 nm.

As seen in FIG. 17, FGF2s which contained in EVs were more stable then naked FGF2s.

INDUSTRIAL APPLICABILITY

A recombinant microorganism according to one embodiment may be used to efficiently isolate EVs or target proteins from the EVs.

According to another embodiment, a composition for delivering the EVs and target proteins to a subject may be used to efficiently deliver the target proteins to a subject.

According to another embodiment, a method of treating a disease of a subject may be used to efficiently treat the disease.

According to another embodiment, a method of applying a cosmetic to a subject may be used to efficiently apply a cosmetic to a subject.

According to another embodiment, a method of producing EVs may be used to efficiently produce EVs.

The invention claimed is:

1. An extracellular vesicle derived from a recombinant microorganism comprising one or more polynucleotides encoding one or more target proteins, wherein the microorganism is a yeast, wherein the extracellular vesicle is an isolated extracellular vesicle, wherein the target protein is linked to a signal peptide, thereby making the microorganism load the target protein into the extracellular vesicle in an increased amount than the target protein not linked to the signal peptide and wherein the signal peptide is encoded by the nucleotide sequence of SEQ ID NO:4 and the extracellular vesicle comprises the target protein.

2. The extracellular vesicle of claim 1, wherein the yeast belongs to the genus selected from the group consisting of *Saccharomyces, Pichia*, and *Hansenula*.

3. The extracellular vesicle of claim 1, wherein the target protein is one or more selected from the group consisting of a growth factor, a cytokine, an antibody, an enzyme, an inhibitory protein, and a fragment thereof.

4. The extracellular vesicle of claim 3, wherein the target protein is one or more selected from the group consisting of a fibroblast growth factor 1 (FGF1), fibroblast growth factor 2 (FGF2), and an epidermal growth factor (EGF), insulin-like growth factor 1 (IGF1), KGF, TGFα, TRX, and IL-22.

5. The extracellular vesicle of claim 1, which has a diameter of about 20 nm to about 500 nm.

6. A composition for delivering a target protein to a subject, comprising the extracellular vesicle of claim 1 as an active ingredient and a carrier.

7. The composition of claim 6, for delivering the target protein transdermally, intradermally, orally, transmucosally, or intramucosally.

8. The composition of claim 6, for use as a pharmaceutical or a cosmetic.

9. The composition of claim 6, for alleviating a skin wrinkle, whitening a skin, blocking ultraviolet rays, or alleviating inflammation.

10. The composition of claim 6, wherein the yeast belongs to the genus selected from the group consisting of *Saccharomyces, Pichia*, and *Hansenula*.

11. The composition of claim 6, wherein the target protein is one or more selected from the group consisting of a growth factor, a cytokine, an antibody, an enzyme, an inhibitory protein, and a fragment thereof.

12. The composition of claim 11, wherein the target protein is one or more selected from the group consisting of a fibroblast growth factor 1 (FGF1), fibroblast growth factor 2 (FGF2), and an epidermal growth factor (EGF), insulin-like growth factor 1 (IGF1), KGF, TGFα, TRX, and IL-22.

13. A method for delivering a target protein to a subject, comprising administering the composition of claim 6 to the subject.

14. The method of claim 13, wherein the composition is administered transdermally, intradermally, orally, transmucosally, or intramucosally.

15. The method of claim 13, wherein the composition is administered thereby alleviating a skin wrinkle, whitening a skin, blocking ultraviolet rays, or alleviating inflammation.

* * * * *

SEQUENCE LISTING

```
<160> NUMBER OF SEQ ID NOS: 60

<210> SEQ ID NO 1
<211> LENGTH: 5778
<212> TYPE: DNA
<213> ORGANISM: Artificial Sequence
<220> FEATURE:
<223> OTHER INFORMATION: pRS416 GPD vector

<400> SEQUENCE: 1
gacgaaaggg cctcgtgata cgcctatttt tataggttaa tgtcatgata ataatggttt      60
cttaggacgg atcgcttgcc tgtaacttac acgcgcctcg tatcttttaa tgatggaata    120
atttgggaat ttactctgtg tttatttatt tttatgtttt gtatttggat tttagaaagt    180
aaataaagaa ggtagaagag ttacggaatg aagaaaaaaa aataaacaaa ggtttaaaaa    240
atttcaacaa aaagcgtact ttacatatat atttattaga caagaaaagc agattaaata    300
gatatacatt cgattaacga taagtaaaat gtaaaatcac aggattttcg tgtgtggtct    360
tctacacaga caagatgaaa caattcggca ttaatacctg agagcaggaa gagcaagata    420
aaaggtagta tttgttggcg atcccctag agtctttac atcttcggaa aacaaaaact    480
attttttctt taatttcttt tttacttc tattttaat ttatatattt atattaaaaa    540
atttaaatta taattatttt tatagcacgt gatgaaaagg acccaggtgg cacttttcgg    600
ggaaatgtgc gcggaacccc tatttgttta ttttctaaa tacattcaaa tatgtatccg    660
ctcatgagac aataaccctg ataaatgctt caataatatt gaaaaaggaa gagtatgagt    720
attcaacatt tccgtgtcgc ccttattccc ttttttgcgg cattttgcct tcctgttttt    780
gctcacccag aaacgctggt gaaagtaaaa gatgctgaag atcagttggg tgcacgagtg    840
ggttacatcg aactggatct caacagcggt aagatccttg agagttttcg ccccgaagaa    900
cgttttccaa tgatgagcac ttttaaagtt ctgctatgtg gcgcggtatt atcccgtatt    960
gacgccgggc aagagcaact cggtcgccgc atacactatt ctcagaatga cttggttgag   1020
tactcaccag tcacagaaaa gcatcttacg gatggcatga cagtaagaga attatgcagt   1080
gctgccataa ccatgagtga taacactgcg gccaacttac ttctgacaac gatcggagga   1140
ccgaaggagc taaccgcttt tttgcacaac atgggggatc atgtaactcg ccttgatcgt   1200
tgggaaccgg agctgaatga agccatacca aacgacgagc gtgacaccac gatgcctgta   1260
gcaatggcaa caacgttgcg caaactatta actggcgaac tacttactct agcttcccgg   1320
caacaattaa tagactggat ggaggcggat aaagttgcag gaccacttct gcgctcggcc   1380
cttccggctg gctggtttat tgctgataaa tctggagccg gtgagcgtgg gtctcgcggt   1440
atcattgcag cactggggcc agatggtaag ccctcccgta tcgtagttat ctacacgacg   1500
gggagtcagg caactatgga tgaacgaaat agacagatcg ctgagatagg tgcctcactg   1560
attaagcatt ggtaactgtc agaccaagtt tactcatata ctttagat tgatttaaaa   1620 cttcattttt aatttaaaag gatctaggtg aagatccttt ttgataatct catgaccaaa   1680
atcccttaac gtgagttttc gttccactga gcgtcagacc ccgtagaaaa gatcaaagga   1740
tcttcttgag atcctttttt tctgcgcgta atctgctgct tgcaaacaaa aaaaccaccg   1800
```

```
ctaccagcgg tggtttgttt gccggatcaa gagctaccaa ctcttttcc gaaggtaact      1860 ggcttcagca gagcgcagat accaaatact gtccttctag tgtagccgta gttaggccac      1920
cacttcaaga actctgtagc accgcctaca tacctcgctc tgctaatcct gttaccagtg      1980
gctgctgcca gtggcgataa gtcgtgtctt accgggttgg actcaagacg atagttaccg      2040
gataaggcgc agcggtcggg ctgaacgggg ggttcgtgca cacagcccag cttggagcga      2100
acgacctaca ccgaactgag atacctacag cgtgagctat gagaaagcgc cacgcttccc      2160
gaagggagaa aggcggacag gtatccggta agcggcaggg tcggaacagg agagcgcacg      2220
agggagcttc caggggggaaa cgcctggtat ctttatagtc ctgtcgggtt tcgccacctc      2280
tgacttgagc gtcgattttt gtgatgctcg tcagggggggc ggagcctatg gaaaaacgcc      2340
agcaacgcgg ccttttttacg gttcctggcc ttttgctggc cttttgctca catgttcttt      2400
cctgcgttat ccctgattc tgtggataac cgtattaccg cctttgagtg agctgatacc      2460
gctcgccgca gccgaacgac cgagcgcagc gagtcagtga gcgaggaagc ggaagagcgc      2520
ccaatacgca aaccgcctct ccccgcgcgt tggccgattc attaatgcag ctggcacgac      2580
aggtttcccg actggaaagc gggcagtgag cgcaacgcaa ttaatgtgag ttacctcact      2640
cattaggcac cccaggcttt acactttatg cttccggctc ctatgttgtg tggaattgtg      2700
agcggataac aatttcacac aggaaacagc tatgaccatg attacgccaa gcgcgcaatt      2760
aaccctcact aaagggaaca aaagctggag ctcagtttat cattatcaat actcgccatt      2820
tcaaagaata cgtaaataat taatagtagt gattttccta actttattta gtcaaaaaat      2880 tagccttta attctgctgt aacccgtaca tgcccaaaat aggggggcggg ttacacagaa      2940 tatataacat cgtaggtgtc tgggtgaaca gtttattcct ggcatccact aaatataatg      3000
gagcccgctt tttaagctgg catccagaaa aaaaagaat cccagcacca aaatattgtt      3060
ttcttcacca accatcagtt cataggtcca ttctcttagc gcaactacag agaacagggg      3120
cacaaacagg caaaaaacgg gcacaacctc aatggagtga tgcaacctgc ctggagtaaa      3180
tgatgacaca aggcaattga cccacgcatg tatctatctc attttcttac acctttctatt      3240 accttctgct ctctctgatt tggaaaaagc tgaaaaaaaa ggttgaaacc agttccctga      3300
aattattccc ctacttgact aataagtata taaagacggt aggtattgat tgtaattctg      3360
taaatctatt tcttaaactt cttaaattct acttttatag ttagtcttt tttttagtttt      3420 aaaacaccag aacttagttt cgacggattc tagaactagt ggatccccg ggctgcagga      3480 attcgatatc aagcttatcg ataccgtcga cctcgagtca tgtaattagt tatgtcacgc      3540
ttacattcac gccctccccc cacatccgct ctaaccgaaa aggaaggagt tagacaacct      3600
gaagtctagg tccctatttta ttttttata gttatgttag tattaagaac gttatttata      3660
tttcaaattt ttctttttt tctgtacaga cgcgtgtacg catgtaacat tatactgaaa      3720
accttgcttg agaaggtttt gggacgctcg aaggctttaa tttgcggccg gtacccaatt      3780
cgccctatag tgagtcgtat tacgcgcgct cactggccgt cgttttacaa cgtcgtgact      3840
gggaaaaccc tggcgttacc caacttaatc gccttgcagc acatccccct ttcgccagct      3900
ggcgtaatag cgaagaggcc cgcaccgatc gcccttccca acagttgcgc agcctgaatg      3960
gcgaatggcg cgacgcgccc tgtagcggcg cattaagcgc ggcgggtgtg gtggttacgc      4020
gcagcgtgac cgctacactt gccagcgccc tagcgcccgc tcctttcgct ttcttccctt      4080
cctttctcgc cacgttcgcc ggctttcccc gtcaagctct aaatcggggg ctccctttag      4140
```

```
ggttccgatt tagtgcttta cggcacctcg accccaaaaa acttgattag ggtgatggtt    4200
cacgtagtgg gccatcgccc tgatagacgg ttttccgccc tttgacgttg gagtccacgt    4260
tctttaatag tggactcttg ttccaaactg gaacaacact caaccctatc tcggtctatt    4320
cttttgattt ataagggatt ttgccgattt cggcctattg gttaaaaaat gagctgattt    4380
aacaaaaatt taacgcgaat tttaacaaaa tattaacgtt tacaatttcc tgatgcggta    4440
ttttctcctt acgcatctgt gcggtatttc acaccgcata gggtaataac tgatataatt    4500
aaattgaagc tctaatttgt gagtttagta tacatgcatt tacttataat acagtttttt    4560
agttttgctg gccgcatctt ctcaaatatg cttcccagcc tgcttttctg taacgttcac    4620
cctctacctt agcatccctt cccttttgcaa atagtcctct tccaacaata ataatgtcag    4680
atcctgtaga gaccacatca tccacggttc tatactgttg acccaatgcg tctcccttgt    4740
catctaaacc cacaccgggt gtcataatca accaatcgta accttcatct cttccaccca    4800
tgtctctttg agcaataaag ccgataacaa aatctttgtc gctcttcgca atgtcaacag    4860
tacccttagt atattctcca gtagatagg agcccttgca tgacaattct gctaacatca    4920
aaaggcctct aggttccttt gttacttctt ctgccgcctg cttcaaaccg ctaacaatac    4980
ctgggcccac cacaccgtgt gcattcgtaa tgtctgccca ttctgctatt ctgtatacac    5040
ccgcagagta ctgcaatttg actgtattac caatgtcagc aaattttctg tcttcgaaga    5100
gtaaaaaatt gtacttggcg gataatgcct ttagcggctt aactgtgccc tccatggaaa    5160
aatcagtcaa gatatccaca tgtgttttta gtaaacaaat tttgggacct aatgcttcaa    5220
ctaactccag taattccttg gtggtacgaa catccaatga agcacacaag tttgtttgct    5280
tttcgtgcat gatattaaat agcttggcag caacaggact aggatgagta gcagcacgtt    5340
ccttatatgt agctttcgac atgatttatc ttcgtttcct gcaggttttt gttctgtgca    5400
gttgggttaa gaatactggg caatttcatg tttcttcaac actacatatg cgtatatata    5460
ccaatctaag tctgtgctcc ttccttcgtt cttccttctg ttcggagatt accgaatcaa    5520
aaaaatttca agaaaccga atcaaaaaa agaataaaa aaaaatgat gaattgaatt    5580 gaaaagctgt ggtatggtgc actctcagta caatctgctc tgatgccgca tagttaagcc    5640
agccccgaca cccgccaaca cccgctgacg cgccctgacg ggcttgtctg ctcccggcat    5700
ccgcttacag acaagctgtg accgtctccg ggagctgcat gtgtcagagg ttttcaccgt    5760
catcaccgaa acgcgcga                                                  5778
```

<210> SEQ ID NO 2
<211> LENGTH: 6606
<212> TYPE: DNA
<213> ORGANISM: Artificial Sequence
<220> FEATURE:
<223> OTHER INFORMATION: pRS426 GPD vector

<400> SEQUENCE: 2

```
gacgaaaggg cctcgtgata cgcctatttt tataggttaa tgtcatgata ataatggttt      60
cttagtatga tccaatatca aaggaaatga tagcattgaa ggatgagact aatccaattg     120
aggagtggca gcatatagaa cagctaaagg gtagtgctga aggaagcata cgatacccg     180 catggaatgg gataatatca caggaggtac tagactacct ttcatcctac ataaatagac     240
gcatataagt acgcatttaa gcataaacac gcactatgcc gttcttctca tgtatatata     300
tatacaggca acacgcagat ataggtgcga cgtgaacagt gagctgtatg tgcgcagctc     360
gcgttgcatt tcggaagcg ctcgtttttcg gaaacgcttt gaagttccta ttccgaagtt     420
```

```
cctattctct agaaagtata ggaacttcag agcgcttttg aaaaccaaaa gcgctctgaa      480
gacgcacttt caaaaaacca aaaacgcacc ggactgtaac gagctactaa aatattgcga      540
ataccgcttc cacaaacatt gctcaaaagt atctctttgc tatatatctc tgtgctatat      600
ccctatataa cctacccatc caccttttcgc tccttgaact tgcatctaaa ctcgacctct     660
acatttttta tgtttatctc tagtattact ctttagacaa aaaaattgta gtaagaacta      720
ttcatagagt gaatcgaaaa caatacgaaa atgtaaacat ttcctatacg tagtatatag      780
agacaaaata gaagaaaccg ttcataattt tctgaccaat gaagaatcat caacgctatc      840
actttctgtt cacaaagtat gcgcaatcca catcggtata aatataatc ggggatgcct       900 ttatcttgaa aaaatgcacc cgcagcttcg ctagtaatca gtaaacgcgg aagtggagt       960 caggcttttt ttatggaaga gaaaatagac accaaagtag ccttcttcta accttaacgg     1020
acctacagtg caaaaagtta tcaagagact gcattataga gcgcacaaag gagaaaaaaa    1080
gtaatctaag atgctttgtt agaaaaatag cgctctcggg atgcattttt gtagaacaaa    1140
aaagaagtat agattctttg ttggtaaaat agcgctctcg cgttgcattt ctgttctgta    1200
aaaatgcagc tcagattctt tgtttgaaaa attagcgctc tcgcgttgca ttttgtttt    1260 acaaaaatga agcacagatt cttcgttggt aaaatagcgc tttcgcgttg catttctgtt   1320
ctgtaaaaat gcagctcaga ttctttgttt gaaaaattag cgctctcgcg ttgcattttt   1380
gttctacaaa atgaagcaca gatgcttcgt tcaggtggca cttttcgggg aaatgtgcgc   1440 ggaacccta tttgtttatt tttctaaata cattcaaata tgtatccgct catgagacaa    1500
taaccctgat aaatgcttca ataatattga aaaggaaga gtatgagtat caacatttc    1560 cgtgtcgccc ttattccctt ttttgcggca ttttgccttc ctgttttgc tcacccagaa   1620 acgctggtga agtaaaaga tgctgaagat cagttgggtg cacgagtggg ttacatcgaa   1680
ctggatctca acagcggtaa gatccttgag agttttcgcc ccgaagaacg ttttccaatg   1740
atgagcactt ttaaagttct gctatgtggc gcggtattat cccgtattga cgccgggcaa   1800
gagcaactcg gtcgccgcat acactattct cagaatgact tggttgagta ctcaccagtc    1860
acagaaaagc atcttacgga tggcatgaca gtaagagaat tatgcagtgc tgccataacc    1920
atgagtgata acactgcggc caacttactt ctgacaacga tcggaggacc gaaggagcta    1980
accgcttttt tgcacaacat gggggatcat gtaactcgcc ttgatcgttg ggaaccggag    2040
ctgaatgaag ccataccaaa cgacgagcgt gacaccacga tgcctgtagc aatggcaaca    2100
acgttgcgca aactattaac tggcgaacta cttactctag cttcccggca acaattaata    2160
gactggatgg aggcggataa agttgcagga ccacttctgc gctcggccct tccggctggc    2220
tggtttattg ctgataaatc tggagccggt gagcgtgggt ctcgcggtat cattgcagca    2280
ctggggccag atggtaagcc ctcccgtatc gtagttatct acacgacggg gagtcaggca    2340
actatggatg aacgaaatag acagatcgct gagataggtg cctcactgat taagcattgg    2400
taactgtcag accaagttta ctcatatata ctttagattg atttaaaact tcatttttaa    2460
tttaaaagga tctaggtgaa gatcctttt gataatctca tgaccaaaat cccttaacgt    2520
gagttttcgt tccactgagc gtcagacccc gtagaaaaga tcaaaggatc ttcttgagat    2580
cctttttttc tgcgcgtaat ctgctgcttg caaacaaaaa aaccaccgct accagcggtg    2640
gtttgtttgc cggatcaaga gctaccaact cttttccga aggtaactgg cttcagcaga    2700
gcgcagatac caaatactgt ccttctagtg tagccgtagt taggccacca cttcaagaac    2760
```

```
tctgtagcac cgcctacata cctcgctctg ctaatcctgt taccagtggc tgctgccagt   2820
ggcgataagt cgtgtcttac cgggttggac tcaagacgat agttaccgga taaggcgcag   2880
cggtcgggct gaacggggggg ttcgtgcaca cagcccagct tggagcgaac gacctacacc   2940
gaactgagat acctcagcgt gagctatga gaaagcgcca cgcttcccga agggagaaag   3000
gcggacaggt atccggtaag cggcagggtc ggaacaggag agcgcacgag ggagcttcca   3060
gggggaaacg cctggtatct ttatagtcct gtcgggtttc gccacctctg acttgagcgt   3120 cgattttgt gatgctcgtc agggggggcgg agcctatgga aaaacgccag caacgcggcc   3180 ttttttacggt tcctggcctt ttgctggcct tttgctcaca tgttctttcc tgcgttatcc   3240
cctgattctg tggataaccg tattaccgcc tttgagtgag ctgataccgc tcgccgcagc   3300
cgaacgaccg agcgcagcga gtcagtgagc gaggaagcgg aagagcgccc aatacgcaaa   3360
ccgcctctcc ccgcgcgttg gccgattcat taatgcagct ggcacgacag gtttcccgac   3420
tggaaagcgg gcagtgagcg caacgcaatt aatgtgagtt acctcactca ttaggcaccc   3480
caggctttac actttatgct tccggctcct atgttgtgtg gaattgtgag cggataacaa   3540
tttcacacag gaaacagcta tgaccatgat tacgccaagc gcgcaattaa ccctcactaa   3600
agggaacaaa agctggagct cagtttatca ttatcaatac tcgccatttc aaagaatacg   3660
taaataatta atagtagtga ttttcctaac ttttatttagt caaaaaatta gccttttaat   3720
tctgctgtaa cccgtacatg cccaaaatag ggggcgggtt acacagaata tataacatcg   3780
taggtgtctg ggtgaacagt ttattcctgg catccactaa atataatgga gcccgctttt   3840
taagctggca tccagaaaaa aaagaatcc cagcaccaaa atattgtttt cttcaccaac   3900
catcagttca taggtccatt ctcttagcgc aactacagag aacaggggca caaacaggca   3960
aaaaacgggc acaacctcaa tggagtgatg caacctgcct ggagtaaatg atgacacaag   4020
gcaattgacc cacgcatgta tctatctcat tttcttacac cttctattac cttctgctct   4080
ctctgatttg gaaaaagctg aaaaaaaagg ttgaaccag ttccctgaaa ttattcccct   4140
acttgactaa taagtatata aagacggtag gtattgattg taattctgta aatctatttc   4200
ttaaacttct taaattctac ttttatagtt agtcttttttt ttagttttaa aacaccagaa   4260
cttagtttcg acggattcta gaactagtgg atccccccggg ctgcaggaat tcgatatcaa   4320
gcttatcgat accgtcgacc tcgagtcatg taattagtta tgtcacgctt acattcacgc   4380 cctccccccca catccgctct aaccgaaaag gaaggagtta gacaacctga gtctaggtc   4440 cctatttatt ttttttatagt tatgttagta ttaagaacgt tatttatatt tcaaattttt   4500 cttttttttttc tgtacagacg cgtgtacgca tgtaacatta tactgaaaac cttgcttgag   4560
aaggttttgg gacgctcgaa ggctttaatt tgcggccggt acccaattcg ccctatagtg   4620
agtcgtatta cgcgcgctca ctggccgtcg ttttacaacg tcgtgactgg gaaaaccctg   4680
gcgttaccca acttaatcgc cttgcagcac atccccctttt cgccagctgg cgtaatagcg   4740
aagaggcccg caccgatcgc ccttcccaac agttgcgcag cctgaatggc gaatggcgcg   4800
acgcgccctg tagcggcgca ttaagcgcgg cgggtgtggt ggttacgcgc agcgtgaccg   4860
ctacacttgc cagcgcccta gcgcccgctc ctttcgcttt cttcccttcc tttctcgcca   4920
cgttcgccgg ctttccccgt caagctctaa atcgggggct ccctttaggg ttccgattta   4980
gtgctttacg gcacctcgac cccaaaaaac ttgattaggg tgatggttca cgtagtgggc   5040
catcgccctg atagacggtt tttcgccctt tgacgttgga gtccacgttc tttaatagtg   5100
gactcttgtt ccaaactgga acaacactca accctatctc ggtctattct tttgatttat   5160
```

| | |
|---|---|
| aagggatttt gccgatttcg gcctattggt taaaaaatga gctgatttaa caaaaattta | 5220 |
| acgcgaattt taacaaaata ttaacgttta caatttcctg atgcggtatt ttctccttac | 5280 |
| gcatctgtgc ggtatttcac accgcatagg gtaataactg ataataattaa attgaagctc | 5340 |
| taatttgtga gtttagtata catgcattta cttataatac agttttttag ttttgctggc | 5400 |
| cgcatcttct caaatatgct tcccagcctg cttttctgta acgttcaccc tctaccttag | 5460 |
| catcccttcc ctttgcaaat agtcctcttc caacaataat aatgtcagat cctgtagaga | 5520 |
| ccacatcatc cacggttcta tactgttgac ccaatgcgtc tcccttgtca tctaaaccca | 5580 |
| caccgggtgt cataatcaac caatcgtaac cttcatctct tccacccatg tctctttgag | 5640 |
| caataaagcc gataacaaaa tctttgtcgc tcttcgcaat gtcaacagta cccttagtat | 5700 |
| attctccagt agatagggag cccttgcatg acaattctgc taacatcaaa aggcctctag | 5760 |
| gttcctttgt tacttcttct gccgcctgct tcaaaccgct aacaatacct gggcccacca | 5820 |
| caccgtgtgc attcgtaatg tctgcccatt ctgctattct gtatacaccc gcagagtact | 5880 |
| gcaatttgac tgtattacca atgtcagcaa attttctgtc ttcgaagagt aaaaaattgt | 5940 |
| acttggcgga taatgccttt agcggcttaa ctgtgccctc catggaaaaa tcagtcaaga | 6000 |
| tatccacatg tgtttttagt aaacaaattt tgggacctaa tgcttcaact aactccagta | 6060 |
| attccttggt ggtacgaaca tccaatgaag cacacaagtt tgtttgcttt tcgtgcatga | 6120 |
| tattaaatag cttggcagca acaggactag gatgagtagc agcacgttcc ttatatgtag | 6180 |
| cttttcgacat gatttatctt cgtttcctgc aggttttttgt tctgtgcagt tgggttaaga | 6240 |
| atactgggca atttcatgtt tcttcaacac tacatatgcg tatatatacc aatctaagtc | 6300 |
| tgtgctcctt ccttcgttct tccttctgtt cggagattac cgaatcaaaa aaatttcaaa | 6360 |
| gaaaccgaaa tcaaaaaaaa gaataaaaaa aaaatgatga attgaattga aaagctgtgg | 6420 |
| tatggtgcac tctcagtaca atctgctctg atgccgcata gttaagccag ccccgacacc | 6480 |
| cgccaacacc cgctgacgcg ccctgacggg cttgtctgct cccggcatcc gcttacagac | 6540 |
| aagctgtgac cgtctccggg agctgcatgt gtcagaggtt ttcaccgtca tcaccgaaac | 6600 |
| gcgcga | 6606 |

<210> SEQ ID NO 3
<211> LENGTH: 644
<212> TYPE: DNA
<213> ORGANISM: Artificial Sequence
<220> FEATURE:
<223> OTHER INFORMATION: Promoter GPD

<400> SEQUENCE: 3

| | |
|---|---|
| tcattatcaa tactcgccat ttcaaagaat acgtaaataa ttaatagtag tgattttcct | 60 |
| aactttattt agtcaaaaaa ttagccttt aattctgctg taacccgtac atgcccaaaa | 120 |
| taggggcgg gttacacaga atatataaca tcgtaggtgt ctgggtgaac agtttattcc | 180 |
| tggcatccac taaatataat ggagcccgct ttttaagctg gcatccagaa aaaaaagaa | 240 |
| tcccagcacc aaaatattgt tttcttcacc aaccatcagt tcataggtcc attctcttag | 300 |
| cgcaactaca gagaacaggg gcacaaacag gcaaaaaacg ggcacaaccct caatggagtg | 360 |
| atgcaacctg cctggagtaa atgatgacac aaggcaattg acccacgcat gtatctatct | 420 |
| cattttctta caccttctat taccttctgc tctctctgat ttggaaaaag ctgaaaaaaa | 480 |
| aggttgaaac cagttccctg aaattattcc cctacttgac taataagtat ataagacgg | 540 |

```
taggtattga ttgtaattct gtaaatctat ttcttaaact tcttaaattc tacttttata    600
gttagtcttt tttttagttt taaaacacca gaacttagtt tcga                    644
```

```
<210> SEQ ID NO 4
<211> LENGTH: 266
<212> TYPE: DNA
<213> ORGANISM: Artificial Sequence
<220> FEATURE:
<223> OTHER INFORMATION: Signal sequence of mating factor alpha

<400> SEQUENCE: 4
atgagatttc cttcaatttt tactgcagtt ttattcgcag catcctccgc attagctgct     60
ccagtcaaca ctacaacaga agatgaaacg gcacaaattc cggctgaagc tgtcatcggt    120
tacttagatt tagaagggga tttcgatgtt gctgttttgc cattttccaa cagcacaaat    180
aacgggttat tgtttataaa tactactatt gccagcattg ctgctaaaga agaaggggta    240
tctttggata aaagagaggc tgaagc                                         266
```

```
<210> SEQ ID NO 5
<211> LENGTH: 159
<212> TYPE: DNA
<213> ORGANISM: Artificial Sequence
<220> FEATURE:
<223> OTHER INFORMATION: codon optimized EFG1

<400> SEQUENCE: 5
aattccgatt ccgagtgccc tctgtcacat gatggatatt gtctacatga cggagtgtgc     60
atgtatatag aagctctgga caagtatgcc tgtaactgtg ttgtcgggta tcggcgag     120 agatgccaat acagggacct aaaatggtgg gaactaagg                            159
```

```
<210> SEQ ID NO 6
<211> LENGTH: 210
<212> TYPE: DNA
<213> ORGANISM: Artificial Sequence
<220> FEATURE:
<223> OTHER INFORMATION: codon optimized IGF1

<400> SEQUENCE: 6
ggccctgaga cattatgtgg tgcggagctt gtcgatgcat acagttcgt atgcggagat      60 agaggcttct atttcaacaa acctacaggc tacggttcca gttccagaag ggcacctcaa    120
actggtatag ttgacgaatg ttgcttcaga agctgcgacc tgagaagact agaaatgtac    180
tgtgcgcccc tgaaaccagc caagagtgca                                     210
```

```
<210> SEQ ID NO 7
<211> LENGTH: 420
<212> TYPE: DNA
<213> ORGANISM: Artificial Sequence
<220> FEATURE:
<223> OTHER INFORMATION: codon optimized FGF1

<400> SEQUENCE: 7
tttaacttgc ctccggggaa ttacaagaag ccgaaattac tgtattgctc aaacggaggc     60
cacttcctga gaatccttcc cgacggtact gttgacggca cgagagaccg tagtgatcaa    120
cacatccagt acaattgag cgccgagagc gtgggagaag tttacataaa gagcacagaa    180
actggccaat accttgcgat ggataccgga gggcttcttt atgggagcca gaccccaaac    240
gaggaatgct atttcttcga aaggctggag gagaatcatt acaatacata tattagtaaa    300
aaacatgcgg aaaagaattg gtttgtcggt ctgaaaaaga acggtagctg caaaagaggt    360
```
cccaggaccc attacgggca gaaggcgata ctatttctgc cgctacccgt ctcctccgac    420

<210> SEQ ID NO 8
<211> LENGTH: 438
<212> TYPE: DNA
<213> ORGANISM: Artificial Sequence
<220> FEATURE:
<223> OTHER INFORMATION: codon optimized FGF2

<400> SEQUENCE: 8
cccgcgctac cagaggacgg tggtagcgga gcattccccc ccggccattt caaagaccca     60
aagagactat attgtaagaa cggcggattt tttctgcgta ttcatcccga cggaagggta    120
gatggggttc gtgagaaaag cgacccgcac attaaacttc agcttcaagc agaagaacgt    180
ggggtagtat ccatcaaagg tgtctgcgct aataggtact tggcgatgaa ggaggacggt    240
agattgcttg cctctaaatg tgtgaccgac gaatgctttt tcttcgagag acttgagtcc    300
aacaactata acatacag aagtcgtaaa tacacctcat ggtacgtggc gttgaaacgt    360
actggtcagt acaagcttgg ttctaaaaca ggaccaggtc aaaaagccat acttttcta    420
ccaatgtctg ccaagtcc                                                 438

<210> SEQ ID NO 9
<211> LENGTH: 489
<212> TYPE: DNA
<213> ORGANISM: Artificial Sequence
<220> FEATURE:
<223> OTHER INFORMATION: codon optimized FGF7

<400> SEQUENCE: 9
tgcaacgaca tgactccaga gcagatggca accaacgtaa actgttcaag cccggagcgt     60
cacacaaggt cctatgatta tatggagggg ggggatattc gtgttaggag actattctgc    120
agaacacaat ggtatctgcg tattgataaa aggggcaagg tcaaaggaac tcaagaaatg    180
aaaaataact ataacattat ggagataaga acggtcgcgg tcgggattgt tgcgattaaa    240
ggcgtggagt ccgaatttta ccttgccatg aataaggaag aaaactgta cgccaagaag    300
gagtgcaacg aggattgtaa ctttaaggag ttgattttgg aaaaccatta caatacttat    360
gccagtgcaa agtggacgca taacggggg gagatgttcg tcgccctgaa tcagaaaggt    420
atacctgttc gtggcaagaa gactaaaaaa gaacaaaaaa cagcacactt tcttccaatg    480
gcgatcact                                                            489

<210> SEQ ID NO 10
<211> LENGTH: 150
<212> TYPE: DNA
<213> ORGANISM: Artificial Sequence
<220> FEATURE:
<223> OTHER INFORMATION: codon optimized TGFalpha

<400> SEQUENCE: 10
gtggtatctc attttaacga ctgccctgat tcacatactc aattttgttt ccacgggact     60
tgcaggttct tggtccaaga agataagccc gcgtgcgttt gccattcagg ttatgttggt    120
gcgaggtgtg aacacgctga cctgcttgct                                    150

<210> SEQ ID NO 11
<211> LENGTH: 315
<212> TYPE: DNA
<213> ORGANISM: Artificial Sequence
<220> FEATURE:

<223> OTHER INFORMATION: codon optimized TRX1 gene

<400> SEQUENCE: 11

```
atggtcaagc aaattgagag caaaacggcg ttccaggaag cactggacgc ggcgggagac    60
aaacttgtag tagtggactt ctccgccaca tggtgcggtc catgcaaaat gatcaaaccg   120
ttcttccatt ccttgagcga aaagtacagc aacgtgatat tcttgaagt ggatgtcgat   180
gactgtcaag acgttgcgtc cgagtgtgaa gttaaatgta tgccaacatt tcagttcttt   240
aagaaaggac agaaggtggg agagttcagc ggcgcaaata agagaaatt agaggcaact   300
attaatgagc tagtg                                                   315
```

<210> SEQ ID NO 12
<211> LENGTH: 50
<212> TYPE: PRT
<213> ORGANISM: Homo sapiens

<400> SEQUENCE: 12

Val Val Ser His Phe Asn Asp Cys Pro Asp Ser His Thr Gln Phe Cys
1               5                   10                  15

Phe His Gly Thr Cys Arg Phe Leu Val Gln Glu Asp Lys Pro Ala Cys
            20                  25                  30

Val Cys His Ser Gly Tyr Val Gly Ala Arg Cys Glu His Ala Asp Leu
        35                  40                  45

Leu Ala
    50

<210> SEQ ID NO 13
<211> LENGTH: 146
<212> TYPE: PRT
<213> ORGANISM: Homo sapiens

<400> SEQUENCE: 13

Pro Ala Leu Pro Glu Asp Gly Gly Ser Gly Ala Phe Pro Pro Gly His
1               5                   10                  15

Phe Lys Asp Pro Lys Arg Leu Tyr Cys Lys Asn Gly Gly Phe Phe Leu
            20                  25                  30

Arg Ile His Pro Asp Gly Arg Val Asp Gly Val Arg Glu Lys Ser Asp
        35                  40                  45

Pro His Ile Lys Leu Gln Leu Gln Ala Glu Glu Arg Gly Val Val Ser
    50                  55                  60

Ile Lys Gly Val Cys Ala Asn Arg Tyr Leu Ala Met Lys Glu Asp Gly
65                  70                  75                  80

Arg Leu Leu Ala Ser Lys Cys Val Thr Asp Glu Cys Phe Phe Phe Glu
                85                  90                  95

Arg Leu Glu Ser Asn Asn Tyr Asn Thr Tyr Arg Ser Arg Lys Tyr Thr
            100                 105                 110

Ser Trp Tyr Val Ala Leu Lys Arg Thr Gly Gln Tyr Lys Leu Gly Ser
        115                 120                 125

Lys Thr Gly Pro Gly Gln Lys Ala Ile Leu Phe Leu Pro Met Ser Ala
    130                 135                 140

Lys Ser
145

<210> SEQ ID NO 14
<211> LENGTH: 53
<212> TYPE: PRT
<213> ORGANISM: Homo sapiens

<400> SEQUENCE: 14

```
Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg
    50
```

<210> SEQ ID NO 15
<211> LENGTH: 70
<212> TYPE: PRT
<213> ORGANISM: Homo sapiens

<400> SEQUENCE: 15

```
Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
    50                  55                  60

Lys Pro Ala Lys Ser Ala
65                  70
```

<210> SEQ ID NO 16
<211> LENGTH: 163
<212> TYPE: PRT
<213> ORGANISM: Homo sapiens

<400> SEQUENCE: 16

```
Cys Asn Asp Met Thr Pro Glu Gln Met Ala Thr Asn Val Asn Cys Ser
1               5                   10                  15

Ser Pro Glu Arg His Thr Arg Ser Tyr Asp Tyr Met Glu Gly Gly Asp
            20                  25                  30

Ile Arg Val Arg Arg Leu Phe Cys Arg Thr Gln Trp Tyr Leu Arg Ile
        35                  40                  45

Asp Lys Arg Gly Lys Val Lys Gly Thr Gln Glu Met Lys Asn Asn Tyr
    50                  55                  60

Asn Ile Met Glu Ile Arg Thr Val Ala Val Gly Ile Val Ala Ile Lys
65                  70                  75                  80

Gly Val Glu Ser Glu Phe Tyr Leu Ala Met Asn Lys Glu Gly Lys Leu
                85                  90                  95

Tyr Ala Lys Lys Glu Cys Asn Glu Asp Cys Asn Phe Lys Glu Leu Ile
            100                 105                 110

Leu Glu Asn His Tyr Asn Thr Tyr Ala Ser Ala Lys Trp Thr His Asn
        115                 120                 125

Gly Gly Glu Met Phe Val Ala Leu Asn Gln Lys Gly Ile Pro Val Arg
    130                 135                 140

Gly Lys Lys Thr Lys Lys Glu Gln Lys Thr Ala His Phe Leu Pro Met
145                 150                 155                 160

Ala Ile Thr
```

```
<210> SEQ ID NO 17
<211> LENGTH: 50
<212> TYPE: PRT
<213> ORGANISM: Homo sapiens

<400> SEQUENCE: 17

Val Val Ser His Phe Asn Asp Cys Pro Asp Ser His Thr Gln Phe Cys
1               5                   10                  15

Phe His Gly Thr Cys Arg Phe Leu Val Gln Glu Asp Lys Pro Ala Cys
            20                  25                  30

Val Cys His Ser Gly Tyr Val Gly Ala Arg Cys Glu His Ala Asp Leu
        35                  40                  45

Leu Ala
    50

<210> SEQ ID NO 18
<211> LENGTH: 105
<212> TYPE: PRT
<213> ORGANISM: Homo sapiens

<400> SEQUENCE: 18

Met Val Lys Gln Ile Glu Ser Lys Thr Ala Phe Gln Glu Ala Leu Asp
1               5                   10                  15

Ala Ala Gly Asp Lys Leu Val Val Asp Phe Ser Ala Thr Trp Cys
            20                  25                  30

Gly Pro Cys Lys Met Ile Lys Pro Phe Phe His Ser Leu Ser Glu Lys
            35                  40                  45

Tyr Ser Asn Val Ile Phe Leu Glu Val Asp Val Asp Asp Cys Gln Asp
50                  55                  60

Val Ala Ser Glu Cys Glu Val Lys Cys Met Pro Thr Phe Gln Phe Phe
65                  70                  75                  80

Lys Lys Gly Gln Lys Val Gly Glu Phe Ser Gly Ala Asn Lys Glu Lys
            85                  90                  95

Leu Glu Ala Thr Ile Asn Glu Leu Val
            100                 105

<210> SEQ ID NO 19
<211> LENGTH: 146
<212> TYPE: PRT
<213> ORGANISM: Homo sapiens

<400> SEQUENCE: 19

Leu Pro Val Asn Thr Arg Cys Lys Leu Glu Val Ser Asn Phe Gln Gln
1               5                   10                  15

Pro Tyr Ile Val Asn Arg Thr Phe Met Leu Ala Lys Glu Ala Ser Leu
            20                  25                  30

Ala Asp Asn Asn Thr Asp Val Arg Leu Ile Gly Glu Lys Leu Phe Arg
            35                  40                  45

Gly Val Ser Ala Lys Asp Gln Cys Tyr Leu Met Lys Gln Val Leu Asn
        50                  55                  60

Phe Thr Leu Glu Asp Val Leu Leu Pro Gln Ser Asp Arg Phe Gln Pro
65                  70                  75                  80

Tyr Met Gln Glu Val Val Pro Phe Leu Thr Lys Leu Ser Asn Gln Leu
            85                  90                  95

Ser Ser Cys His Ile Ser Gly Asp Asp Gln Asn Ile Gln Lys Asn Val
            100                 105                 110

Arg Arg Leu Lys Glu Thr Val Lys Lys Leu Gly Glu Ser Gly Glu Ile
            115                 120                 125
```

Lys Ala Ile Gly Glu Leu Asp Leu Leu Phe Met Ser Leu Arg Asn Ala
            130                 135                 140

Cys Val
145

<210> SEQ ID NO 20
<211> LENGTH: 4271
<212> TYPE: DNA
<213> ORGANISM: Artificial Sequence
<220> FEATURE:
<223> OTHER INFORMATION: pMT182-PR4

<400> SEQUENCE: 20

| | | | | | | |
|---|---|---|---|---|---|---|
| ggtacctccg | cttcctcgct | cactgactcg | ctgcgctcgg | tcgttcggct | gcggcgagcg | 60 |
| gtatcagctc | actcaaaggc | ggtaatacgg | ttatccacag | aatcagggga | taacgcagga | 120 |
| aagaacatgt | gagcaaaagg | ccagcaaaag | gccaggaacc | gtaaaaaggc | cgcgttgctg | 180 |
| gcgtttttcc | ataggctccg | cccccctgac | gagcatcaca | aaaatcgacg | ctcaagtcag | 240 |
| aggtggcgaa | acccgacagg | actataaaga | taccaggcgt | ttccccctgg | aagctccctc | 300 |
| gtgcgctctc | ctgttccgac | cctgccgctt | accggatacc | tgtccgcctt | tctcccttcg | 360 |
| ggaagcgtgg | cgctttctca | tagctcacgc | tgtaggtatc | tcagttcggt | gtaggtcgtt | 420 |
| cgctccaagc | tgggctgtgt | gcacgaaccc | cccgttcagc | ccgaccgctg | cgccttatcc | 480 |
| ggtaactatc | gtcttgagtc | aacccggta | agacacgact | tatcgccact | ggcagcagcc | 540 |
| actggtaaca | ggattagcag | agcgaggtat | gtaggcggtg | ctacagagtt | cttgaagtgg | 600 |
| tggcctaact | acggctacac | tagaagaaca | gtatttggta | tctgcgctct | gctgaagcca | 660 |
| gttaccttcg | gaaaaagagt | tggtagctct | tgatccggca | aacaaaccac | cgctggtagc | 720 |
| ggtggttttt | ttgtttgcaa | gcagcagatt | acgcgcagaa | aaaaaggatc | tcaagaagat | 780 |
| cctttgatct | tttctacggg | gtctgacgct | cagtggaacg | aaaactcacg | ttaagggatt | 840 |
| ttggtcatga | gattatcaaa | aaggatcttc | acctagatcc | ttttaaatta | aaaatgaagt | 900 |
| tttaaatcaa | tctaaagtat | atatgagtaa | acttggtgaa | ttcgcaaggt | atagcccaat | 960 |
| atactttact | tcgtaaagtt | tgagctctgc | gaggcaaaaa | cgtcagatat | tgaatctaaa | 1020 |
| caagagtata | ataaacacag | ttacacaaat | aaaaacaaaa | ggagtagatc | ttaaaaatgg | 1080 |
| aagcaaatcc | aaagtggcaa | gaaacaggaa | gacaacaaaa | agtaaaacaa | cttgactatt | 1140 |
| cagaaacatt | agcagtaaga | atagacaatg | tggaattata | caactcagaa | aagaaattat | 1200 |
| attatctagt | aattcaaacc | cttcttggga | atccccaaaa | aaatgaatgg | cgtatccagg | 1260 |
| gacaaagtca | atatattaaaa | gaatcaaaac | aaaaaataat | tgtgtcataa | aattattgca | 1320 |
| cattaaaagt | cctaaaaatt | attttgcatt | aaagatttca | aaactcattt | aatgtaaaat | 1380 |
| aattttttct | ttgataatcc | catttagcaa | caatctcgcg | taccacttgg | tcaaccttt | 1440 |
| gatcatcact | atccgtatta | atcaaatcac | cattctcaac | gtcttctaat | tgcaactgct | 1500 |
| tgcgaatttc | tttcagcaaa | ccgccatagc | taatttgccg | ggaaccagcc | aaagctcgtt | 1560 |
| ccaaatcatc | aattacttgt | aggtcttgtt | cttgattatt | agtcaaaata | tctttagatt | 1620 |
| ttacctgata | tttagccgtt | tcttgagcac | tagccaataa | cgaattttta | tggcgattca | 1680 |
| tattcggttt | aactgcctca | acattcacca | ttggtacata | agtcaatttc | attgcccgtt | 1740 |
| gccaaaaacc | agtccattct | acttgtgaaa | tatagttatc | agtccccta | aaataatggt | 1800 |
| tcttcacaaa | aagcaaaaca | tgcatatgat | ggtggtacat | tggctgaccc | gcttcatgat | 1860 |

```
taacagtcac ttcagtcgaa cgtacatagc ccaataaatt tttggcaact tttgtatact    1920
gaaaaatttt tgcaacagct cgtcccattt gacgtaactc actcttcaat tgatcaccag    1980
ttgtattctc aaccgtcaac gttaaaaata agaaccggcc cgtctttcgt tgtttaacag    2040
cttccgtcaa aatctgtgtt aactgattgg attgcttcat tgcccgccgc caattacata    2100
acggacacaa acgagaatgg caaaaccaag tctgcgccaa tttcttgtga ccatttttat    2160
cttccacaaa acgcaaaact tcgccacatt ctttaactcg atgagctttc ttataatgca    2220
atatttgtaa atagtcacca tactgcaagt tctccaactt gcgctcccgc cacggccgaa    2280 cttttccctga ctttgaccga tcaaccaaga cttttttcatt agccaaaata aaaactcccc    2340
tcaccaacca cgtgagaaga gttaatctgt tatgtacttg cttcacttaa atcagtcaga    2400
aggcttgacg gcaaagggtt caagctttaa actatgtcta gtaaatccaa atacgatttt    2460
tacaagatta actcacgcgt tcgaggtcgg caaactttcg aagctcacgt gggttttttt    2520
tatatttatt ttataccaca ataatacgcc taaacccagt tgtgtcaagg gtttacctca    2580 cttttttgaaa atgacgttgt ttctaatagt atcaagataa gaagaaaccg tcgaaaaaac    2640
gacggtttca aaccccaaaa agcagagaat tcggtacctg gagctgtaat ataaaaacct    2700
tcttcaacta acggggcagg ttagtgacat tagaaaaccg actgtaaaaa gtacagtcgg    2760
cattatctca tattataaaa gccagtcatt aggcctatct gacaattcct gaatagagtt    2820
cataaacaat cctgcatgat aaccatcaca acagaatga tgtacctgta agatagcgg    2880 taaatatatt gaattacctt tattaatgaa ttttcctgct gtaataatgg gtagaaggta    2940
attactatta ttattgatat ttaagttaaa cccagtaaat gaagtccatg gaataataga    3000
aagagaaaaa gcattttcag gtataggtgt tttgggaaac aatttccccg aaccattata    3060
tttctctaca tcagaaaggt ataaatcata aaactctttg aagtcattct ttacaggagt    3120
ccaaatacca gagaatgttt tagatacacc atcaaaaatt gtataaagtg gctctaactt    3180
atcccaataa cctaactctc cgtcgctatt gtaaccagtt ctaaaagctg tatttgagtt    3240 tatcacccttt gtcactaaga aaataaatgc agggtaaaat ttatatcctt cttgttttat    3300
gtttcggtat aaaacactaa tatcaatttc tgtggttata ctaaaagtcg tttgttggtt    3360
caaataatga ttaaatatct cttttctctt ccaattgtct aaatcaattt tattaaagtt    3420
catttgatat gcctcctaaa tttttatcta aagtgaattt aggaggctta cttgtctgct    3480
ttcttcatta gaatcaatcc ttttttaaaa gtcaatatta ctgtaacata aatatatatt    3540
ttaaaaatat cccactttat ccaattttcg tttgttgaac taatgggtgc tttagttgaa    3600
gaataaagac cacattaaaa aatgtggtct aagcttctgc aggatatccg atcgtccaca    3660
atcaaggtgc ttggctttttt cgatcgcgag gtcaccatgt acatcagtcg tgagagcatt    3720
gtgttgacag tgatcggcat cgtgttcggc tatctgctcg gcaatttgct gacagcctac    3780
attttgtatc aagccgaaac tgaggccgtg gttttttccac tcacgatcag cattgtcggc    3840
tacctcacgg ccacgttact catgttggcc ttcaccggcg tcgtcacctg gctcacgcat    3900
cgtcgactcc aacgggtgga catggtcgaa gccctgaaat caaacgaata acctacaatt    3960
ttgtcaggca gcgtcgtcac ggcgctgctt ttttcataca aaattcatca aaaattggga    4020
ttaaaaacgt tcatgatcgc aattttgaag cgcaaatgaa gattgagacc aactcctaac    4080
agtcctgtaa cgctgacgta acattgacac agtaaagtag cctttagtta atcaaattaa    4140
gggtgaggtc aaaaatgaaa ttcaataaag tcatgatcac gttggttgct gcagttacct    4200
tagcaggttc tgctagcgcc gtaacaccag ttttcgctga tacaagcgga tcctctagaa    4260
```

-continued tcgatctcga g                                                          4271

<210> SEQ ID NO 21
<211> LENGTH: 31
<212> TYPE: PRT
<213> ORGANISM: Artificial Sequence
<220> FEATURE:
<223> OTHER INFORMATION: Signal peptide SP4

<400> SEQUENCE: 21

Met Lys Phe Asn Lys Val Met Ile Thr Leu Val Ala Ala Val Thr Leu
1               5                   10                  15

Ala Gly Ser Ala Ser Ala Val Thr Pro Val Phe Ala Asp Thr Ser
            20                  25                  30

<210> SEQ ID NO 22
<211> LENGTH: 30
<212> TYPE: PRT
<213> ORGANISM: Artificial Sequence
<220> FEATURE:
<223> OTHER INFORMATION: Signal peptide1

<400> SEQUENCE: 22

Met Lys Lys Leu Leu Ser Thr Val Leu Phe Ser Ala Val Ala Leu Ser
1               5                   10                  15

Ala Val Ala Leu Ser Lys Pro Ser His Val Ser Ala Ala Thr
            20                  25                  30

<210> SEQ ID NO 23
<211> LENGTH: 27
<212> TYPE: PRT
<213> ORGANISM: Artificial Sequence
<220> FEATURE:
<223> OTHER INFORMATION: Signal peptide2

<400> SEQUENCE: 23

Met Lys Lys Phe Leu Val Ser Val Gly Leu Leu Gly Met Leu Val Leu
1               5                   10                  15

Ser Thr Gly Ala Val Thr Ala His Ala Ala Asp
            20                  25

<210> SEQ ID NO 24
<211> LENGTH: 27
<212> TYPE: PRT
<213> ORGANISM: Artificial Sequence
<220> FEATURE:
<223> OTHER INFORMATION: Signal peptide3

<400> SEQUENCE: 24

Met Lys Lys Lys Ile Ile Ser Ala Ile Leu Met Ser Thr Val Ile Leu
1               5                   10                  15

Ser Ala Ala Ala Pro Leu Ser Gly Val Tyr Ala
            20                  25

<210> SEQ ID NO 25
<211> LENGTH: 28
<212> TYPE: PRT
<213> ORGANISM: Artificial Sequence
<220> FEATURE:
<223> OTHER INFORMATION: Signal peptide4

<400> SEQUENCE: 25

Met Lys Asn Lys Leu Leu Met Ser Leu Val Leu Val Cys Ala Phe Leu
1               5                   10                  15

```
Gly Ile Ala Gly Ala His Thr Val His Ala Ala Asp
            20                  25
```

```
<210> SEQ ID NO 26
<211> LENGTH: 30
<212> TYPE: PRT
<213> ORGANISM: Artificial Sequence
<220> FEATURE:
<223> OTHER INFORMATION: Signal peptide5

<400> SEQUENCE: 26

Met Lys Lys Thr Thr Leu Leu Leu Ser Thr Leu Phe Leu Gly Gly Thr
1               5                   10                  15

Leu Leu Ala Thr Thr Leu Ala Thr Pro Val Val Ala Asp Thr
            20                  25                  30
```

```
<210> SEQ ID NO 27
<211> LENGTH: 20
<212> TYPE: PRT
<213> ORGANISM: Artificial Sequence
<220> FEATURE:
<223> OTHER INFORMATION: Yeast Signal peptide1

<400> SEQUENCE: 27

Met Ile Leu His Thr Tyr Ile Ile Leu Ser Leu Leu Thr Ile Phe Pro
1               5                   10                  15

Lys Ala Ile Gly
            20
```

```
<210> SEQ ID NO 28
<211> LENGTH: 22
<212> TYPE: PRT
<213> ORGANISM: Artificial Sequence
<220> FEATURE:
<223> OTHER INFORMATION: Yeast Signal peptide2

<400> SEQUENCE: 28

Met Phe Ser Pro Ile Leu Ser Leu Glu Ile Ile Leu Ala Leu Ala Thr
1               5                   10                  15

Leu Gln Ser Val Phe Ala
            20
```

```
<210> SEQ ID NO 29
<211> LENGTH: 40
<212> TYPE: PRT
<213> ORGANISM: Artificial Sequence
<220> FEATURE:
<223> OTHER INFORMATION: Yeast Signal peptide3

<400> SEQUENCE: 29

Met Lys Ile Leu Ser Ala Leu Leu Leu Phe Thr Leu Ala Phe Ala
1               5                   10                  15

Glu Val Ile Glu Leu Thr Asn Lys Asn Phe Asp Asp Val Val Leu Lys
            20                  25                  30

Ser Gly Lys Tyr Thr Leu Val Lys
            35                  40
```

```
<210> SEQ ID NO 30
<211> LENGTH: 40
<212> TYPE: PRT
<213> ORGANISM: Artificial Sequence
<220> FEATURE:
<223> OTHER INFORMATION: Yeast Signal peptide4
```

```
<400> SEQUENCE: 30

Met Lys Phe Ala Tyr Ser Leu Leu Pro Leu Ala Gly Val Ser Ala
1               5                   10                  15

Ser Val Ile Asn Tyr Lys Arg Asp Gly Asp Ser Lys Ala Ile Thr Asn
            20                  25                  30

Thr Thr Phe Ser Leu Asn Arg Pro
            35                  40

<210> SEQ ID NO 31
<211> LENGTH: 40
<212> TYPE: PRT
<213> ORGANISM: Artificial Sequence
<220> FEATURE:
<223> OTHER INFORMATION: Yeast Signal peptide4

<400> SEQUENCE: 31

Met Lys Ala Phe Thr Ser Leu Leu Cys Gly Leu Gly Leu Ser Thr Thr
1               5                   10                  15

Leu Ala Lys Ala Ile Ser Leu Gln Arg Pro Leu Gly Leu Asp Lys Asp
            20                  25                  30

Val Leu Leu Gln Ala Ala Glu Lys
            35                  40

<210> SEQ ID NO 32
<211> LENGTH: 19
<212> TYPE: PRT
<213> ORGANISM: Artificial Sequence
<220> FEATURE:
<223> OTHER INFORMATION: Yeast Signal peptide5

<400> SEQUENCE: 32

Met Arg Phe Pro Ser Ile Phe Thr Ala Val Leu Phe Ala Ala Ser Ser
1               5                   10                  15

Ala Leu Ala

<210> SEQ ID NO 33
<211> LENGTH: 22
<212> TYPE: PRT
<213> ORGANISM: Artificial Sequence
<220> FEATURE:
<223> OTHER INFORMATION: Yeast Signal peptide7

<400> SEQUENCE: 33

Met Phe Tyr Asn Arg Trp Leu Gly Thr Trp Leu Ala Met Ser Ala Leu
1               5                   10                  15

Ile Arg Ile Ser Val Ser
            20

<210> SEQ ID NO 34
<211> LENGTH: 22
<212> TYPE: PRT
<213> ORGANISM: Artificial Sequence
<220> FEATURE:
<223> OTHER INFORMATION: Yeast Signal peptide8

<400> SEQUENCE: 34

Met Thr Leu Ser Phe Ala His Phe Thr Tyr Leu Phe Thr Ile Leu Leu
1               5                   10                  15

Gly Leu Thr Asn Ile Ala
            20

<210> SEQ ID NO 35
```

```
<211> LENGTH: 18
<212> TYPE: PRT
<213> ORGANISM: Artificial Sequence
<220> FEATURE:
<223> OTHER INFORMATION: Yeast Signal peptide9

<400> SEQUENCE: 35

Met Gln Leu Leu Arg Cys Phe Ser Ile Phe Ser Val Ile Ala Ser Val
1               5                   10                  15

Leu Ala

<210> SEQ ID NO 36
<211> LENGTH: 17
<212> TYPE: PRT
<213> ORGANISM: Artificial Sequence
<220> FEATURE:
<223> OTHER INFORMATION: Yeast Signal peptide10

<400> SEQUENCE: 36

Met Leu Lys Ser Ala Val Tyr Ser Ile Leu Ala Ala Ser Leu Val Asn
1               5                   10                  15

Ala

<210> SEQ ID NO 37
<211> LENGTH: 19
<212> TYPE: PRT
<213> ORGANISM: Artificial Sequence
<220> FEATURE:
<223> OTHER INFORMATION: Yeast Signal peptide11

<400> SEQUENCE: 37

Met Phe Thr Phe Leu Lys Ile Ile Leu Trp Leu Phe Ser Leu Ala Leu
1               5                   10                  15

Ala Ser Ala

<210> SEQ ID NO 38
<211> LENGTH: 18
<212> TYPE: PRT
<213> ORGANISM: Artificial Sequence
<220> FEATURE:
<223> OTHER INFORMATION: Yeast Signal peptide12

<400> SEQUENCE: 38

Met Phe Ala Phe Tyr Phe Leu Thr Ala Cys Ile Ser Leu Lys Gly Val
1               5                   10                  15

Phe Gly

<210> SEQ ID NO 39
<211> LENGTH: 21
<212> TYPE: PRT
<213> ORGANISM: Artificial Sequence
<220> FEATURE:
<223> OTHER INFORMATION: Yeast Signal peptide13

<400> SEQUENCE: 39

Met Lys Leu Lys Thr Val Arg Ser Ala Val Leu Ser Ser Leu Phe Ala
1               5                   10                  15

Ser Gln Val Leu Gly
            20

<210> SEQ ID NO 40
<211> LENGTH: 22
<212> TYPE: PRT
<213> ORGANISM: Artificial Sequence
```

```
<220> FEATURE:
<223> OTHER INFORMATION: Yeast Signal peptide14

<400> SEQUENCE: 40

Met Lys Leu Ser Val Leu Thr Phe Val Val Asp Ala Leu Leu Val Cys
1               5                   10                  15

Ser Ser Ile Val Asp Ala
            20

<210> SEQ ID NO 41
<211> LENGTH: 20
<212> TYPE: PRT
<213> ORGANISM: Artificial Sequence
<220> FEATURE:
<223> OTHER INFORMATION: Yeast Signal peptide15

<400> SEQUENCE: 41

Met Lys Leu Gln Leu Ala Ala Val Ala Thr Leu Ala Val Leu Thr Ser
1               5                   10                  15

Pro Ala Phe Gly
            20

<210> SEQ ID NO 42
<211> LENGTH: 22
<212> TYPE: PRT
<213> ORGANISM: Artificial Sequence
<220> FEATURE:
<223> OTHER INFORMATION: Yeast Signal peptide16

<400> SEQUENCE: 42

Met Phe Tyr Asn Arg Trp Leu Gly Thr Trp Leu Ala Met Ser Ala Leu
1               5                   10                  15

Ile Arg Ile Ser Val Ser
            20

<210> SEQ ID NO 43
<211> LENGTH: 25
<212> TYPE: PRT
<213> ORGANISM: Artificial Sequence
<220> FEATURE:
<223> OTHER INFORMATION: Yeast Signal peptide17

<400> SEQUENCE: 43

Met Leu Ser Phe Thr Thr Lys Asn Ser Phe Arg Leu Leu Leu Leu Ile
1               5                   10                  15

Leu Ser Cys Ile Ser Thr Ile Arg Ala
            20                  25

<210> SEQ ID NO 44
<211> LENGTH: 20
<212> TYPE: PRT
<213> ORGANISM: Artificial Sequence
<220> FEATURE:
<223> OTHER INFORMATION: Yeast Signal peptide18

<400> SEQUENCE: 44

Met Lys Phe Ser Thr Ala Leu Ser Val Ala Leu Phe Ala Leu Ala Lys
1               5                   10                  15

Met Val Ile Ala
            20

<210> SEQ ID NO 45
<211> LENGTH: 24
<212> TYPE: PRT
```

```
<213> ORGANISM: Artificial Sequence
<220> FEATURE:
<223> OTHER INFORMATION: Yeast Signal peptide19

<400> SEQUENCE: 45

Met Lys Ile Phe Asn Thr Ile Gln Ser Val Leu Phe Ala Ala Phe Phe
1               5                   10                  15

Leu Lys Gln Gly Asn Cys Leu Ala
            20

<210> SEQ ID NO 46
<211> LENGTH: 20
<212> TYPE: PRT
<213> ORGANISM: Artificial Sequence
<220> FEATURE:
<223> OTHER INFORMATION: Yeast Signal peptide20

<400> SEQUENCE: 46

Met Ser Leu Leu Tyr Ile Ile Leu Leu Phe Thr Gln Phe Leu Leu Leu
1               5                   10                  15

Pro Thr Asp Ala
            20

<210> SEQ ID NO 47
<211> LENGTH: 23
<212> TYPE: PRT
<213> ORGANISM: Artificial Sequence
<220> FEATURE:
<223> OTHER INFORMATION: Yeast Signal peptide21

<400> SEQUENCE: 47

Met Arg Phe Ser Thr Thr Leu Ala Thr Ala Ala Thr Ala Leu Phe Phe
1               5                   10                  15

Thr Ala Ser Gln Val Ser Ala
            20

<210> SEQ ID NO 48
<211> LENGTH: 21
<212> TYPE: PRT
<213> ORGANISM: Artificial Sequence
<220> FEATURE:
<223> OTHER INFORMATION: Yeast Signal peptide22

<400> SEQUENCE: 48

Met Gln Arg Pro Phe Leu Leu Ala Tyr Leu Val Leu Ser Leu Leu Phe
1               5                   10                  15

Asn Ser Ala Leu Gly
            20

<210> SEQ ID NO 49
<211> LENGTH: 32
<212> TYPE: PRT
<213> ORGANISM: Artificial Sequence
<220> FEATURE:
<223> OTHER INFORMATION: Yeast Signal peptide23

<400> SEQUENCE: 49

Met Asn Leu Lys Gln Phe Thr Cys Leu Ser Cys Ala Gln Leu Leu Ala
1               5                   10                  15

Ile Leu Leu Phe Ile Phe Ala Phe Phe Pro Arg Lys Ile Val Leu Thr
            20                  25                  30

<210> SEQ ID NO 50
<211> LENGTH: 19
```

```
<212> TYPE: PRT
<213> ORGANISM: Artificial Sequence
<220> FEATURE:
<223> OTHER INFORMATION: Yeast Signal peptide24

<400> SEQUENCE: 50

Met Leu Leu Gln Ala Phe Leu Phe Leu Leu Ala Gly Phe Ala Ala Lys
1               5                   10                  15

Ile Ser Ala

<210> SEQ ID NO 51
<211> LENGTH: 19
<212> TYPE: PRT
<213> ORGANISM: Artificial Sequence
<220> FEATURE:
<223> OTHER INFORMATION: Yeast Signal peptide25

<400> SEQUENCE: 51

Met Lys Val Arg Lys Tyr Ile Thr Leu Cys Phe Trp Trp Ala Phe Ser
1               5                   10                  15

Thr Ser Ala

<210> SEQ ID NO 52
<211> LENGTH: 21
<212> TYPE: PRT
<213> ORGANISM: Artificial Sequence
<220> FEATURE:
<223> OTHER INFORMATION: Yeast Signal peptide26

<400> SEQUENCE: 52

Met Ile Leu Leu His Phe Val Tyr Ser Leu Trp Ala Leu Leu Leu Ile
1               5                   10                  15

Pro Leu Thr Asn Ala
            20

<210> SEQ ID NO 53
<211> LENGTH: 23
<212> TYPE: PRT
<213> ORGANISM: Artificial Sequence
<220> FEATURE:
<223> OTHER INFORMATION: signal peptide

<400> SEQUENCE: 53

Met Lys Lys Lys Met Arg Leu Lys Val Leu Leu Ala Ser Thr Ala Thr
1               5                   10                  15

Ala Leu Leu Leu Leu Ser Gly
            20

<210> SEQ ID NO 54
<211> LENGTH: 33
<212> TYPE: PRT
<213> ORGANISM: Artificial Sequence
<220> FEATURE:
<223> OTHER INFORMATION: signal peptide

<400> SEQUENCE: 54

Met Gln Arg Lys Lys Lys Gly Leu Ser Ile Leu Leu Ala Gly Thr Val
1               5                   10                  15

Ala Leu Gly Ala Leu Ala Val Leu Pro Val Gly Glu Ile Gln Ala Lys
            20                  25                  30

Ala

<210> SEQ ID NO 55
```

```
<211> LENGTH: 19
<212> TYPE: PRT
<213> ORGANISM: Artificial Sequence
<220> FEATURE:
<223> OTHER INFORMATION: signal peptide

<400> SEQUENCE: 55

Met Lys Lys Trp Phe Ile Ala Leu Ala Gly Leu Leu Leu Thr Val Thr
1               5                   10                  15

Leu Ala Gly

<210> SEQ ID NO 56
<211> LENGTH: 22
<212> TYPE: PRT
<213> ORGANISM: Artificial Sequence
<220> FEATURE:
<223> OTHER INFORMATION: signal peptide

<400> SEQUENCE: 56

Met Lys Lys Tyr Arg Lys Ile Leu Ala Met Leu Ala Val Leu Ala Ile
1               5                   10                  15

Val Leu Val Leu Ser Gly
            20

<210> SEQ ID NO 57
<211> LENGTH: 28
<212> TYPE: PRT
<213> ORGANISM: Artificial Sequence
<220> FEATURE:
<223> OTHER INFORMATION: signal peptide

<400> SEQUENCE: 57

Met Asn Asn Ala Leu Ser Phe Glu Gln Gln Phe Thr Asp Phe Ser Thr
1               5                   10                  15

Leu Ser Asp Ser Glu Leu Glu Ser Val Glu Gly Gly
            20                  25

<210> SEQ ID NO 58
<211> LENGTH: 22
<212> TYPE: PRT
<213> ORGANISM: Artificial Sequence
<220> FEATURE:
<223> OTHER INFORMATION: signal peptide

<400> SEQUENCE: 58

Met Lys Ser Lys Lys Gly Leu Thr Leu Thr Ile Thr Leu Gly Thr Leu
1               5                   10                  15

Ala Leu Phe Leu Ser Gly
            20

<210> SEQ ID NO 59
<211> LENGTH: 21
<212> TYPE: PRT
<213> ORGANISM: Artificial Sequence
<220> FEATURE:
<223> OTHER INFORMATION: signal peptide

<400> SEQUENCE: 59

Met Asp Lys Ile Ile Lys Phe Gln Gly Ile Ser Asp Asp Gln Leu Asn
1               5                   10                  15

Ala Val Ile Gly Gly
            20

<210> SEQ ID NO 60
```

```
<211> LENGTH: 30
<212> TYPE: PRT
<213> ORGANISM: Artificial Sequence
<220> FEATURE:
<223> OTHER INFORMATION: Signal peptide

<400> SEQUENCE: 60

Met Gln Ser Ser Leu Lys Lys Ser Leu Tyr Leu Gly Leu Ala Ala Leu
1               5                   10                  15

Ser Phe Ala Gly Val Ala Ala Val Ser Thr Thr Ala Ser Ala
            20                  25                  30
```